United States Patent
Auberson et al.

(10) Patent No.: US 10,450,298 B2
(45) Date of Patent: Oct. 22, 2019

(54) PET IMAGING AGENTS

(71) Applicants: Yves Auberson, Allschwil (CH); Emmanuelle Briard, Saint-Louis (FR); Darren Le Grand, West Sussex (GB); Berndt Oberhauser, Riehen (CH)

(72) Inventors: Yves Auberson, Allschwil (CH); Emmanuelle Briard, Saint-Louis (FR); Darren Le Grand, West Sussex (GB); Berndt Oberhauser, Riehen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/544,850

(22) PCT Filed: Jan. 20, 2016

(86) PCT No.: PCT/IB2016/050276
§ 371 (c)(1),
(2) Date: Jul. 19, 2017

(87) PCT Pub. No.: WO2016/116875
PCT Pub. Date: Jul. 28, 2016

(65) Prior Publication Data
US 2018/0273509 A1    Sep. 27, 2018

Related U.S. Application Data

(60) Provisional application No. 62/105,336, filed on Jan. 20, 2015.

(51) Int. Cl.
| C07D 401/14 | (2006.01) |
| C07D 413/12 | (2006.01) |
| A61K 51/04  | (2006.01) |
| C07D 401/12 | (2006.01) |
| C07B 59/00  | (2006.01) |
| C07D 413/14 | (2006.01) |

(52) U.S. Cl.
CPC ........ *C07D 401/14* (2013.01); *A61K 51/0459* (2013.01); *C07B 59/002* (2013.01); *C07D 401/12* (2013.01); *C07D 413/12* (2013.01); *C07D 413/14* (2013.01); *C07B 2200/05* (2013.01)

(58) Field of Classification Search
CPC .............................. A61K 51/00; A61K 51/04
See application file for complete search history.

(56) References Cited

FOREIGN PATENT DOCUMENTS

| WO | 2005/043300 A2 | 5/2005 |
| WO | 2005/105770 A2 | 11/2005 |
| WO | 2005/121094 A1 | 12/2005 |
| WO | 2012/020567 A1 | 2/2012 |
| WO | 2014/097151 A2 | 6/2014 |
| WO | WO2014097151 | * 6/2014 |
| WO | 2015/008230 A1 | 1/2015 |

OTHER PUBLICATIONS

Registry No. 1646906-62-8, Entered STN: Feb. 12, 2015.
Registry No. 1646784-61-3, Entered STN: Feb. 12, 2015.
Registry No. 1622624-81-0, Entered STN: Sep. 12, 2014.
Registry No. 1427739-36-3, Entered STN: Apr. 10, 2013.
Registry No. 1349351-32-1, Entered STN: Dec. 6, 2011.
Registry No. 1320808-97-6, Entered STN: Aug. 21, 2011.
Registry No. 1320207-93-9, Entered STN: Aug. 19, 2011.
Registry No. 1011421-82-1, Entered STN: Apr. 1, 2008.
Registry No. 956811-10-2, Entered STN: Dec. 5, 2007.
Registry No. 731830-19-6, Entered STN: Aug. 24, 2004.
Registry No. 731800-55-8, Entered STN: Aug. 24, 2004.
Registry No. 731007-04-8, Entered STN: Aug. 23, 2004.
Registry No. 730944-15-7, Entered STN: Aug. 23, 2004.
Registry No. 1646798-45-9, Entered STN: Feb. 12, 2015.

* cited by examiner

*Primary Examiner* — Michael G. Hartley
*Assistant Examiner* — Jagadishwar R Samala
(74) *Attorney, Agent, or Firm* — Laura K. Madden; Novartis Institutes for Biomedical Research, Inc.

(57) ABSTRACT

Preparation of novel 2-benzyl-5-methyl-2H-tetrazole derivatives of the formula (I) for use as PET imaging agents. The present invention relates to novel compounds of formula (I) their preparation and use as PET imaging agents for imaging techniques and diagnostics in the field of diseases and disorders mediated by or related to the enzyme autotaxin.

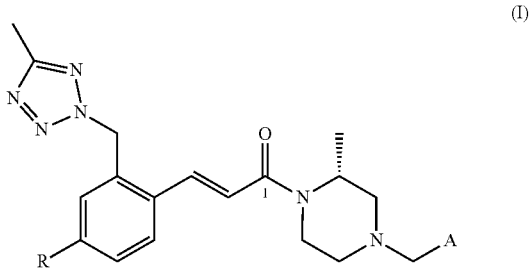

12 Claims, No Drawings

PET IMAGING AGENTS

SUMMARY

This application relates to novel compounds, in particular novel radioactive compounds, salts of such compounds, their preparation, and the use of such novel radioactive compounds as radiotracers/markers for imaging techniques and diagnostics tools in the field of diseases or disorders mediated by and/or related to the enzyme autotaxin, such as fibrogenesis, pruritus, cirrhosis, cancer, neuropathic pain and kidney disease.

Autotaxin (ATX), also known as ectonucleotide pyrophosphatase/phosphodiesterase (ENPP2), is a secreted ectoenzyme known to possess lysophospholipase D activity (Umezu-Goto et al., 2002), and is responsible for producing the bioactive lipid mediator lysophosphatidic acid (LPA) by the hydrolysis of lysophosphatidylcholine (LPC) (Tokumura et al., 2002). LPA is highly implicated in the pathogenesis of a number of physio-pathological diseases, including cancer (Liu et al., 2009; Mills & Moolenaar, 2003), neuropathic pain (Inoue et al., 2004) and fibrosis (Tager et al., 2008). Following the production of LPA, the lipid binds to specific G protein-coupled receptors of which there are seven known isoforms (Noguchi et al., 2009). Binding of LPA activates multiple signalling pathways (Mills & Moolenaar, 2003) including cell migration (van Dijk et al., 1998), proliferation and survival (Brindley, 2004). Other cellular responses include smooth muscle contraction, apoptosis and platelet aggregation (Tigyi & Parrill, 2003).

ATX was originally identified as a cell motility-stimulating factor following isolation from human A2058 melanoma cells (Stracke et al., 1992). Subsequent work on the enzyme was focused towards its role as a motility factor due to its aberrant expression in many cancer types including breast and renal cancer (Stassar et al., 2001), Hodgkin's lymphoma (Baumforth et al., 2005), follicular lymphoma (Masuda et al., 2008), as well as fibrosis of the lung and kidney (Hama et al., 2004). Ten years following its discovery, ATX was characterised as a secreted lysophospholipase (lysoPLD) (Tokumura et al., 2002; Gesta et al., 2002). Since then ATX gene knockout mice have shown that the ATX-LPA signalling axis plays a vital role during embryonic development of the cardiovascular and neural system (Tanaka et al., 2006; van Meeteren et al., 2006), resulting in early embryonic lethality (Bachner et al., 1999).

ATX belongs to a family of proteins called nucleotide pyrophosphatase/phosphodiesterase (NPP), encoded for by the gene ENPP. The family consists of seven structurally related enzymes (ENPP 1-7) conserved within vertebrates which are numbered according to their discovery. They were originally defined by their ability to hydrolyse pyrophosphate or phosphodiester bonds of various nucleotides and nucleotides derivatives in vitro (Stefan et al., 1999; Goding et al., 1998; Gijsbers et al., 2001), though ENPP2 and choline phosphate esters (ENPP6 & 7) have specific activity for other extracellular non-nucleotide molecules. ENPP2 (ATX) is unique within the family as it is the only secreted protein, whereas other ENPP members are transmembrane proteins (Stefan et al., 2005).

Noninvasive nuclear imaging techniques can be used to obtain basic and diagnostic information about the physiology and biochemistry of living subjects, including experimental animals, patients and volunteers. These techniques rely on the use of imaging instruments that can detect radiation emitted from radiotracers administered to living subjects. The information obtained can be reconstructed to provide planar and tomographic images, which reveal the distribution and/or concentration of the radiotracer as a function of time.

Positron emission tomography (PET) is the noninvasive imaging technique that offers the highest spatial and temporal resolution of all nuclear medicine imaging modalities and has the additional advantage that it can allow for the true quantification of tracer concentrations in tissues. The technique involves the use of radiotracers labelled with positron emitting radionuclides that are designed to have in vivo properties, which permit the measurement of parameters regarding the physiology or biochemistry of a variety of processes in living tissue.

Positron emission tomography (PET) is a nuclear medicine, functional imaging technique that produces a three-dimensional image of functional processes in the body. The system detects pairs of gamma rays emitted indirectly by a positron-emitting radionuclide (tracer), which is introduced into the body on a biologically active molecule. Three-dimensional images of tracer concentration within the body are then constructed by computer analysis. In modern PET-CT scanners, three dimensional imaging is often accomplished with the aid of a CT X-ray scan performed on the patient during the same session, in the same machine.

Radionuclides used in PET scanning are typically isotopes with short half-lives such as carbon-11 (~20 min), nitrogen-13 (~10 min), oxygen-15 (~2 min), fluorine-18 (~110 min), or rubidium-82 (~1.27 min). These radionuclides are incorporated either into compounds normally used by the body such as glucose (or glucose analogues), water, or ammonia, or into molecules that bind to receptors or other sites of drug action. Such labelled compounds are known as radiotracers. PET technology can be used to trace the biologic pathway of any compound in living humans (and many other species as well), provided it can be radiolabeled with a PET isotope. Thus, the specific processes that can be probed with PET are virtually limitless.

Due to the short half-lives of most positron-emitting radioisotopes, the radiotracers have traditionally been produced using a cyclotron in close proximity to the PET imaging facility. The half-life of fluorine-18 is long enough that radiotracers labeled with fluorine-18 can be manufactured commercially at offsite locations and shipped to imaging centers.

Single-photon emission computed tomography (SPECT) is nuclear medicine imaging technique similar to PET. It also uses a radioactively labeled tracer and is based on the detection of gamma rays. In contrast to PET, the radioactive label used in SPECT, e.g. $^{123}$I, emits a gamma radiation that is measured directly. We have now found that certain radiolabelled compounds can be used to probe autotaxin in vitro and in vivo using autoradiographic techniques or molecular imaging modalities, such as PET or SPECT. The compounds described herein can be labelled with electron, positron or gamma emitting radioisotopes such as those described above, including, but not limited to, $^{3}$H, $^{13}$N, $^{11}$C, $^{14}$C, $^{18}$F, $^{123}$I, $^{124}$I, $^{125}$I, and/or $^{131}$I.

DESCRIPTION

In a first aspect, this application provides a compound of the general Formula (I)

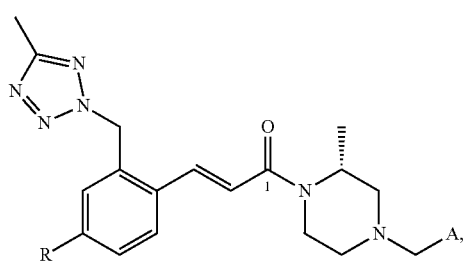

and/or a pharmaceutically acceptable salt thereof, wherein

R is halogen, —CF$_3$, —OCF$_3$, —OCH$_3$, —CH$_3$ or CN; and

A is a pyridinyl or oxazolyl group substituted with at least one substituent selected from halo-(C$_{1-6}$-alkyl), halo-(C$_{1-3}$-alkyl)oxy(C$_{2-4}$-alkyl), or halo-(C$_{1-3}$-alkyl)oxy(C$_{2-4}$-alkyl)oxy(C$_{2-4}$-alkyl).

In another aspect, this application provides a compound of Formula I that optionally contains $^3$H.

In another aspect, this application provides a compound of Formula I, wherein R is —CF$_3$ or —OCF$_3$ and wherein each of these groups may optionally contain at least one $^{18}$F.

In yet another aspect, this application provides a compound of Formula I, where "halo" or "halogen" is a moiety selected from F, Br, Cl, or I. In still another aspect, halo or halogen is selected from $^{18}$F, $^{19}$F, $^{123}$I, $^{124}$I, $^{125}$I or $^{131}$I.

In a further aspect, this application provides a compound of Formula I, where the carbon atom numbered "1" is selected from $^{11}$C, $^{12}$C or $^{14}$C.

The compounds disclosed herein are autotaxin inhibitors. In their non-radioactive form (i.e. when only containing $^{12}$C, $^{19}$F or $^{127}$I), these compounds may be used as therapeutic agents for diseases where autotaxin is involved. In their radiolabeled form, the compounds of the invention may be used as diagnostic agents, for imaging or for radiotherapy. More specifically, in their $^3$H-, $^{11}$C-, $^{14}$C, $^{18}$F-, $^{123}$I-, $^{124}$I-, $^{125}$I- or $^{131}$I-radiolabeled form, the compounds described herein can be used for diagnostic or imaging, or as radiotherapy agents. In particular, $^3$H- and $^{14}$C-radiolabeled derivatives may be used for in vitro and ex vivo radioligand binding assays or autoradiography. $^{11}$C-, $^{18}$F-, $^{123}$I- and $^{124}$I-radiolabeled derivatives may additionally be suitable for in vivo imaging using SPECT (single photon computer tomography) or PET (positron emission tomography), e.g. to image autotaxin protein concentration, or to measure the occupancy of the binding site by a molecule binding to autotaxin. $^{131}$I-radiolabeled derivatives may be suitable as imaging agents and for radiotherapy, e.g. for the treatment of autotaxin-expressing tumors.

Applications of radiolabelled autotaxin ligands may include, but are not limited to clinical studies to quantify autotaxin protein concentration in tissues, to stage or monitor disease progression, or to measure the effect of a therapeutic treatment on autotaxin protein expression (see e.g. Hepatology 2012 56(4):1391-400 for the link between ATX expression and pruritus of cholestasis). Radiolabelled autotaxin ligands may also be used ex vivo or in vivo to determine the receptor occupancy of a drug binding to autotaxin, as well as to image tumors associated with autotaxin-expressing cells, e.g. human hepatocellular carcinoma (see e.g. Molecular Cancer 2010, 9:71).

In accordance with the above, the present application provides agents for use as markers or radiotherapeutic agents for cancer imaging, or agents used for monitoring therapies and diseases in which autotaxin is involved, for instance pruritus of cholestasis, cirrhosis, diabetes, kidney diseases, pain, organ fibrosis, e.g. idiopathic pulmonary fibrosis.

According to another aspect, there is provided a method for detection of autotaxin in a subject in recognized need thereof, comprising: (i) administration of a compound of formula (I) as described anywhere herein, or a pharmaceutically acceptable salt thereof, to said subject; and (ii) detecting uptake of said compound by in vivo PET or SPECT imaging. It is believed that the method will provide information and data having utility in the diagnosis and clinical research of disorders in which autotaxin is involved. In one embodiment the subject is a mammal, most suitably a human who has or is suspected of having a disorder in which autotaxin is involved. The method may be performed quantitatively such that the amount or change in amount of autotaxin, or the density or change in density of autotaxin may be determined so as to diagnose or track progress of a disease. Alternatively the method may be used to locate autotaxin in vivo.

In another further aspect, there is provided a method for quantification of the percentage or change in percentage of unbound autotaxin in a subject after administration of a ligand binding to autotaxin, comprising:
(i) administration of a radiolabeled compound of formula (I) as defined above, or a salt or solvate thereof to said subject;
(ii) detecting uptake of said radiolabeled compound of formula (I) administered in step (i) by in vivo PET or SPECT imaging;
(iii) allowing a suitable amount of time to pass such that the compound administered in step (i) has radioactively decayed; then (iv) administration of an effective amount of either (a) a non-radiolabelled autotaxin ligand, or (b) a non-radiolabelled agent influencing the endogenous level of autotaxin substrates, and contemporaneous administration of a radiolabeled compound of formula (I) or a pharmaceutically acceptable salt thereof as defined in step (i); and (v) detecting uptake of said compound of formula (I) administered in step (iv) by in vivo PET or SPECT imaging.

The time allowed to pass in step (iii) is suitably over 4 times the radioactive isotope half-life, more suitably at least 6 times the radioactive isotope half-life, and more suitably is such that the PET or SPECT signal from the radiolabeled compound of formula (I) administered in step (i) is no longer detectable.

In a still further aspect, there is provided a method for detection of autotaxin in a subject in recognized need thereof, comprising: (i) administration of a radiolabeled compound of formula (I) as described anywhere in this application, or a pharmaceutically acceptable salt thereof to said subject;
(ii) detecting uptake of said radiolabeled compound of formula (I) administered in step (i) by in vivo PET or SPECT imaging;
(iii) administration of an effective amount of either (a) a non-radiolabelled autotaxin ligand, or (b) a non-radiolabelled agent influencing the endogenous level of autotaxin substrates; and
(iv) detecting uptake of said compound of formula (I) administered in step (i) by in vivo PET or SPECT imaging.

A PET or SPECT imaging experiment will provide a three-dimensional image of the distribution of radioactivity, after tracer injection (e.g., a suitably labelled compound of Formula I) in a naïve or pre-treated animal or human subject.

Briefly, after labeling with a radioisotope suitable for PET or SPECT imaging (e.g. 11C, 18F or 123I), the compound of the invention will be injected into the blood circulation of a naïve or pre-treated animal or human subject. After an optional waiting period allowing the molecule to distribute in the body, the subject will be placed into a PET or SPECT scanner, and an image of radioactivity distribution will be reconstructed after recording of a sufficient number of disintegration events. To aid interpretation, a Magnetic Resonance Imaging or Computed Tomography X-ray scan may be performed in parallel to the PET or SPECT scan. To measure target expression (e.g. to study a disease where autotaxin is involved, or to detect autotaxin-expressing tumors), the radiolabeled compound may be injected without pre-treatment of therapy. To measure autotaxin occupancy by a drug binding to autotaxin, or to measure the effect of a therapy on autotaxin expression, the radiolabelled compound will be injected after drug treatment or after therapy and compare to baseline, i.e. the radioactivity signal observed before drug treatment of therapy.

In addition, the distribution of radioactivity derived from a labelled compound of Formula I can be measured by ex-vivo or in vitro autoradiography. As a general example, an animal is injected with a radiolabeled compound of Formula I (with or without pretreatment by a drug or therapy) and subsequently sacrificed. The whole animal or an organ of interest is then frozen or embedded, sliced, and an image is produced after application of the slice against a radiographic film or an imaging plate, e.g. using a photostimulable phosphor plate and creating an image with a phosphor imager.

EXPERIMENTAL SECTION

Examples

The following examples are intended to illustrate the invention and are not to be construed as being limitations thereon.

General Conditions:

Mass spectra were acquired on LC-MS, SFC-MS, or GC-MS systems using electrospray, chemical and electron impact ionization methods from a range of instruments of the following configuration: Agilent 1100 HPLC systems with an Agilent 6110 Mass Spectrometer. [M+H]$^+$ refers to the protonated molecular ion of the chemical species.

NMR spectra were acquired on a Bruker AVANCE 400 MHz or 500 MHz or 600 MHz NMR spectrometers using ICON-NMR, under TopSpin program control. Spectra were measured at 298K, unless indicated otherwise, and were referenced relative to the solvent resonance.

Instrumentation:

MS Methods: Agilent 1100 HPLC systems with an Agilent 6110 Mass Spectrometer 2 minLowpthr03:
Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 5% B, 0.2-1.8 min 5-98% B, 1.8-2.1 min 98% B, 2.1-2.3 min 98% B 2 minLowpHv01:
Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 5% B, 0.2-1.55 min 5-98% B, 1.55-1.75 min 98% B, 1.75-1.8 min 98-5% B 2 minLowpH:
Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 5% B, 0.2-1.3 min 5-98% B, 1.3-1.55 min 98% B, 1.55-1.6 min 98-5% B 10 minLowpH:
Column: Waters Acquity CSH 1.7 μm, 2.1×100 mm
Temperature: 50° C.
Mobile Phase: A: Water+0.1% Formic Acid B: Acetonitrile+0.1% Formic Acid
Flow rate: 0.7 mL/min
Gradient: 0.0 min 2% B, 0.5-8.0 min 2-98% B, 8.0-9.0 min 98% B, 9.0-9.1 min 98-2% B 2 minHighpliv03:
Column: Waters Acquity CSH 1.7 μm, 2.1×50 mm
Temperature: 50° C.
Mobile Phase: A: Water+0.1% Ammonia B: Acetonitrile+0.1% Ammonia
Flow rate: 1.0 mL/min
Gradient: 0.0 min 5% B, 0.2-1.8 min 5-98% B, 1.8-2.1 min 98% B, 2.1-2.3 min 98-5% B 2 min Final Analysis:
Column: Waters Acquity HSS 1.8 μm, 2.1×50 mm
Temperature: 60° C.
Mobile Phase: A: Water+0.05% Formic Acid B: Acetonitrile+0.04% Formic Acid
Flow rate: 1 mL/min
Gradient: from 5 to 98% B in 1.4 min Analytical HPLC:
Column: Zorbax XDB–C18 5μ, 150×4.6 mm
Temperature: 40° C.
Mobile Phase: A: Water+0.01% TFA B: Acetonitrile/MeOH (1:1)
Flow rate: 1 mL/min
Gradient: from 5 to 95% B in 5 min Abbreviations:
BOC tertiary butyl carboxy
br broad
d doublet
dd doublet of doublets
DCM dichloromethane
DIPEA diethylisopropylamine
DMA N,N-dimethylformamide
DME 1,4-dimethoxyethane
DMF N,N-dimethylformamide
DMSO dimethylsulfoxide
EtOAc ethyl acetate
h hour(s)
HPLC high pressure liquid chromatography
LCMS liquid chromatography and mass spectrometry
MeOH methanol
MS mass spectrometry
m or mult multiplet
mg milligram
min minutes
mL milliliter
mmol millimol
MTBE methyl tertiary-butyl ether m/z mass to charge ratio
NMR nuclear magnetic resonance
ppm parts per million
rac racemic
Rt retention time
s singlet
t triplet
TBME methyl tert-butyl ether
TFA trifluoroacetic acid
THF tetrahydrofuran Preparation of Intermediates Intermediate A (R,E)-3-(4-chloro-2-((5-methyl-2H-tetrazol-2-yl)methyl)phenyl)-1-(2-methylpiperazin-1-yl)prop-2-en-1-one

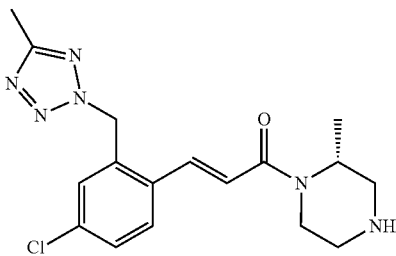 [SMILES: Cc1nnn(Cc2cc(Cl)ccc2/C=C/C(=O)N2CCNC[C@H]2C)n1]

Step 1:
2-(2-Bromo-5-chlorobenzyl)-5-methyl-2H-tetrazole

5-Methyl-2H-tetrazole (77 g, 913 mmol) was placed in a flask with dry DMF (400 mL) at 0° C. using an ice bath. Potassium carbonate (168 g, 1217 mmol) was added in portions followed by dropwise addition of 1-bromo-2-(bromomethyl)-4-chlorobenzene (173 g, 608 mmol) in DMF (400 mL). The resulting mixture was stirred at room temperature for 2 h. The mixture was poured into water and the resulting suspension was collected by filtration. The solid was triturated with iso-hexane and the undissolved solid was removed by filtration. The filtrate was concentrated under reduced pressure giving a white solid which was suspended in water and stirred overnight. The product was filtered and washed with water to afford the title compound.

LCMS: Rt 1.15 min; MS m/z 289.0 [M+H]+; 2 min-LowpHv01

Step 2: (E)-Ethyl 3-(4-chloro-2-((5-methyl-2H-tetrazol-2-yl)methyl)phenyl)acrylate 2-(2-Bromo-5-chlorobenzyl)-5-methyl-2H-tetrazole (15 g, 52.2 mmol), tri-o-tolylphosphine (0.794 g, 2.61 mmol) and triethylamine (10.56 g, 104 mmol) were placed in a flask with dry, degassed DMF (80 mL). Ethyl acrylate (7.83 g, 78 mmol) was added followed by palladium diacetate (0.586 g, 2.61 mmol) and the reaction mixture was stirred at 100° C. overnight. The mixture was allowed to cool, diluted with EtOAc (150 mL) and filtered to remove solids. The reaction mixture was partitioned between EtOAc and water. The organic phase was washed with water and brine, dried over MgSO$_4$, filtered, and the solvent was removed in vacuo. When 75% of the solvent was removed, a solid precipitated out which was collected by filtration and dried to afford the title compound as a white solid.

$^1$H NMR (400 MHz, DMSO-d6) δ7.92 (1H, d), 7.89 (1H, d), 7.59 (1H, d), 7.51 (1H, d of d), 6.59 (1H, d), 6.09 (2H, s), 4.20 (2H, q), 2.41 (3H, s), 1.26 (3H, t).

Step 3: (E)-3-(4-Chloro-2-((5-methyl-2H-tetrazol-2-yl)methyl)phenyl)acrylic acid (E)-Ethyl 3-(4-chloro-2-((5-methyl-2H-tetrazol-2-yl)methyl)phenypacrylate (8.75 g, 28.5 mmol) was placed in a flask with EtOH (100 mL). 2M NaOH (57.1 mL, 114 mmol) was added and the reaction mixture was stirred at room temperature overnight. The ethanol was removed in vacuo and the reaction mixture was acidified with 2M aq. HCl. The resulting precipitate was collected by filtration, washed with water and dried to afford the title compound as a white solid.

LCMS: Rt 0.99 min; MS m/z 279.2 [M+H]+; Method 2 minLowpHv01

Step 4: (R,E)-tert-Butyl 4-(3-(4-chloro-2-((5-methyl-2H-tetrazol-2-yl)methyl)phenypacryloyl)-3-methylpiperazine-1-carboxylate To (E)-3-(4-chloro-2-((5-methyl-2H-tetrazol-2-yl)methyl)phenyl)acrylic acid (1.29 g, 4.63 mmol) in NMP (15 mL) was added HATU (2.112 g, 5.55 mmol) and the mixture was stirred at room temperature for 5 minutes. (R)-tert-Butyl 3-methylpiperazine-1-carboxylate (0.927 g, 4.63 mmol) was added followed by DIPEA (1.617 mL, 9.26 mmol) and the reaction was stirred at room temperature for 2 h. The reaction mixture was poured into water and extracted with EtOAc. The organic portion was washed with water, sat. aq. sodium bicarbonate, water, brine, and dried over a phase separator. The solvent was removed under reduced pressure. Purification of the crude product by chromatography on silica using a gradient from 0-100% EtOAc in iso-hexane afforded the title compound.

LC-MS: Rt=1.23 min; [M+H]$^+$461.3, Method 2 min-LowpH.

Step 5: (R,E)-3-(4-Chloro-2-((5-methyl-2H-tetrazol-2-yl)methyl)phenyl)-1-(2-methylpiperazin-1-yl)prop-2-en-1-one To (R,E)-tert-butyl-4-(3-(4-chloro-2-((5-methyl-2H-tetrazol-2-yl)methyl)phenypacryloyl)-3-methylpiperazine-1-carboxylate (2.1 g, 4.56 mmol) in DCM (22 mL) was added TFA (4.21 mL, 54.7 mmol) and the mixture was stirred at room temperature for 4 h. The solvent was removed under reduced pressure. The resulting residue was loaded onto an Isolute® SCX-2 cartridge eluting with MeOH followed by 2M NH$_3$ in MeOH. The fractions were concentrated under reduced pressure to afford the title compound.

LC-MS: Rt=2.40 min; [M+H]$^+$=361.6, Method 10 min-LowpH.

Intermediate B (R,E)-3-(2-((5-methyl-2H-tetrazol-2-yl)methyl)-4-(trifluoromethyl)phenyl)-1-(2-methylpiperazin-1-yl)prop-2-en-1-one

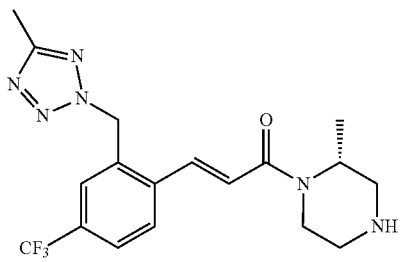 [SMILES: Cc1nnn(Cc2cc(C(F)(F)F)ccc2/C=C/C(=O)N2CCNC[C@H]2C)n1]

Step 1: 2-(2-Bromo-5-(trifluoromethyl)benzyl)-5-methyl-2H-tetrazole

To a stirred solution of 5-methyl-2H-tetrazole (19.44 g, 231 mmol) in DMF (154 mL) at 10° C. under $N_2$ was added $K_2CO_3$ (42.6 g, 308 mmol). The resulting suspension was cooled to −2° C. (ice salt bath) and a solution of 1-bromo-2-(bromomethyl)-4-(trifluoromethyl)benzene (49 g, 154 mmol) in DMF (66 mL) was added dropwise over 30 min keeping the internal temperature below 5° C. On complete addition, the mixture was allowed to warm to room temperature and the resulting white suspension stirred overnight. Water (400 mL) was added slowly to the mixture which was then extracted with EtOAc (2×500 mL). The combined organic extracts were washed with brine (500 mL), dried ($MgSO_4$) and concentrated in vacuo to yield colorless oil. Iso-hexane (150 mL) was added and the resulting slurry was filtered and the solid washed with iso-hexane (2×50 mL). The filtrate was concentrated in vacuo to yield a colourless oil. Purification by chromatography on silica eluting with 0-50% EtOAc in iso-hexane afforded the title compound.

LCMS: Rt 1.30 min; MS m/z 321.3 [M+H]+; Method 2 minLowpHv03

Step 2: (E)-Ethyl-3-(2-((5-methyl-2H-tetrazol-2-yl)methyl)-4-(trifluoromethyl)phenyl)acrylate To a stirred solution of 2-(2-bromo-5-(trifluoromethyl)benzyl)-5-methyl-2H-tetrazole (17 g, 52.9 mmol) in DMF (76 mL) was added tri-o-tolylphosphine (0.806 g, 2.65 mmol) and triethylamine (14.76 mL, 106 mmol). The solution was de-gassed by bubbling $N_2$ through it for 20 mins. $Pd(OAc)_2$ (0.594 g, 2.65 mmol) and ethyl acrylate (8.66 mL, 79 mmol) were added and the reaction mixture heated to 90° C. under $N_2$. After cooling to room temperature, the mixture was partitioned between water (150 mL) and EtOAc (250 mL). The phases were separated and the aqueous phase extracted with more EtOAc (250 mL). The combined organic layers were washed with brine (2×250 mL), dried ($MgSO_4$) and concentrated in vacuo to yield the title compound as orange oil.

LCMS: Rt 1.36 min; MS m/z 341.5 [M+H]+; Method 2 minLowpHv03

Step 3: (E)-3-(2-((5-Methyl-2H-tetrazol-2-yl)methyl)-4-(trifluoromethyl)phenyacrylic acid To a stirred solution of crude (E)-ethyl 3-(2-((5-methyl-2H-tetrazol-2-yl)methyl)-4-(trifluoromethyl)phenypacrylate (18.02 g, assume 53.0 mmol) in EtOH (212 mL) was added 2M aq. NaOH (79 mL, 159 mmol) slowly. The resulting orange solution was stirred at room temperature overnight. The resulting mixture was concentrated in vacuo to a volume of 100 ml and then filtered. 5M HCl (38 mL) was added slowly to adjust the pH to 2 whereupon a solid started to crystallize out of solution. The mixture was stirred at room temperature for 2 h to allow full crystallization. The resulting slurry was filtered, and the filter cake washed with 50% aq. EtOH (2×20 mL). The solid was dried in vacuo at 40° C. overnight to afford the title compound.

LCMS: Rt 1.14 min; MS m/z 313.4[M+H]+; Method 2 minLowpHv03

Step 4: (R,E)-tert-Butyl 3-methyl-4-(3-(2-((5-methyl-2H-tetrazol-2-yl)methyl)-4-(trifluoromethyl)phenyl)acryloyl)piperazine-1-carboxylate T3P® 50% in ethyl acetate (4.5 mL, 7.7 mmol) was added to a solution of (E)-3-(4-(difluoromethyl)-2-((5-methyl-2H-tetrazol-2-yl)methyl)phenyl)acrylic acid (2 g, 6.41 mmol), (R)-tert-butyl 3-methylpiperazine-1-carboxylate (2.0 g, 6.4 mmol) and TEA (3.6 mL, 25.6 mmol) in DCM (20 mL) and the resulting mixture stirred for 1 h at room temperature. The reaction mixture was diluted with sat. aq. sodium bicarbonate (100 mL) The aqueous solution was extracted with ethyl acetate (3×100 mL). The combined organic solutions were washed with water (50 mL), brine (50 mL), dried over sodium sulphate, filtered and concentrated in vacuo. Purification was performed by silica gel column chromatography eluting with a gradient of iso-hexane to ethyl acetate. The product fractions were combined and evaporated in vacuo to give a white solid.

LC MS: Rt 1.39 min; [M−100+H]+395.3, Method 2 minLowpHv03

Step 5: (R,E)-3-(2-((5-Methyl-2H-tetrazol-2-yl)methyl)-4-(trifluoromethyl)phenyl)-1-(2-methylpiperazin-1-yl)prop-2-en-1-one TFA (10 mL) was added to a solution of (R,E)-tert-butyl 2-(3-methyl-4-(3-(2-((5-methyl-2H-tetrazol-2-yl)methyl)-4-(trifluoromethyl)phenypacryloyl)piperazin-1-yl)acetate (2.7 g, 5.46 mmol) in DCM (10 mL) and the resulting mixture stirred for 1 h. Toluene (100 mL) was added and the reaction concentrated in vacuo. The resulting gum was stirred in diethyl ether (250 mL), water (1 mL) was added and the resulting solid was collected by filtration, washed with ether and dried under vacuum to give the title compound as a trifluoroacetate salt.

LC MS: Rt 0.74 min; [M+H]+395.0, 397.5, Method 2 minLowpHv03

Intermediate C 5-(2-(2-fluoroethoxy)ethoxy)picolinaldehyde

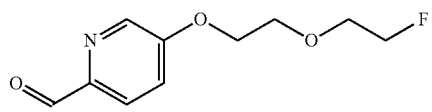 [SMILES: O=Cc1ccc(OCCOCCF)cn1]

Step 1: 2-(2-((6-methylpyridin-3-yl)oxy)ethoxy)ethanol

A suspension of 6-methylpyridin-3-ol (1.5 g, 13.75 mmol), diethylene glycol monochlorohydrin (5.83 mL, 55.0 mmol), K$_2$CO$_3$ (2.85 g, 20.62 mmol) and NaI (0.11 g, 0.76 mmol) in DMF (18.6 mL) was stirred at 85° C. for 16 h under an argon atmosphere. The reaction mixture was allowed to cool to RT, diluted with EtOAc and washed twice with water. The aqueous layer was extracted with DCM/i-PrOH (4/1). The combined organic layers were washed with brine, dried over a phase separator and concentrated. The combined organic layers were dried and concentrated to give crude product as a purple oil which was purified by flash chromatography DCM/MeOH (100/0 to 90/10) to afford 5.0 g of a brown oil.

LC MS: Rt 0.32 min; [M+H]$^+$198.1; 2 min Final Analysis

Step 2: 2-(2-((6-methylpyridin-3-yl)oxy)ethoxy) ethyl 4-methylbenzenesulfonate

To a stirred solution of 2-(2-((6-methylpyridin-3-yl)oxy)ethoxy)ethanol (2.35 g, 4.05 mmol) in CH$_2$Cl$_2$ (10 mL) was slowly added p-tolylsulfonyl chloride (1.87 g, 9.72 mmol) followed by triethylamine (2.82 mL, 20.26 mmol) at 0° C., under argon. The reaction mixture was stirred at RT for 16 h. The reaction mixture was diluted with CH$_2$Cl$_2$ and water. The organic layer was washed with brine, dried over a phase separator and concentrated to give the crude product as an brown oil, which was purified by flash chromatography (cyclohexane/EtOAc, from 100/0 to 0/100) to afford 1.02 g of the desired product as a yellow oil.

LC MS: Rt 0.85 min; [M+H]$^+$352.4; 2 min Final Analysis

Step 3: 5-(2-(2-fluoroethoxy)ethoxy)-2-methylpyridine

To a solution of 2-(2-((6-methylpyridin-3-yl)oxy)ethoxy) ethyl 4-methylbenzenesulfonate (1.02 g, 2.48 mmol) in THF (15.7 mL) was added TBAF (1M in THF) (12.40 mL, 12.40 mmol) and the resulting solution was stirred at 65° C. for 30 min. The solvent was evaporated, and the residue taken up in EtOAc and washed with water. The aqueous layer was extracted twice with EtOAc. The combined organic layers were washed with brine, dried over a phase separator and concentrated to the give crude product as a brown oil, which was purified by flash chromatography (cyclohexane/EtOAc: 100/0 to 0/100) to afford the title compound as an orange oil (465 mg).

$^1$H NMR (400 MHz, DMSO-d6) δ ppm 2.41 (s, 3H) 3.64-3.72 (m, 1H) 3.76-3.83 (m, 3H) 4.16 (dd, J=5.44, 3.73 Hz, 2H) 4.45-4.53 (m, 1H) 4.61-4.64 (m, 1H) 7.18 (d, J=8.56 Hz, 1H) 7.31 (dd, J=8.50, 3.00 Hz, 1H) 8.17 (d, J=2.93 Hz, 1H) LC MS: Rt 0.44 min; [M+H]$^+$200.1; 2 min Final Analysis Step 4: 5-(2-(2-fluoroethoxy)ethoxy)-2-methylpyridine 1-oxide To a solution of 5-(2-(2-fluoroethoxy)ethoxy)-2-methylpyridine (465 mg, 2.1 mmol) in CHCl$_3$ (10.6 mL) at 0° C. was added m-chloroperbenzoic acid (435 mg, 2.52 mmol). The resulting mixture was stirred at 0° C. for 3 h. The reaction mixture was quenched with a saturated solution of Na$_2$CO$_3$ and extracted twice with CH$_2$Cl$_2$. The combined organic layers were washed with brine, dried over a phase separator and concentrated to give 562 mg of crude product as yellow oil.

LC MS: Rt 0.48 min; [M+H]$^+$216.1; 2 min Final Analysis

Step 5: (5-(2-(2-fluoroethoxy)ethoxy)pyridin-2-yl) methyl acetate

To acetic anhydride (2018 µl, 21.39 mmol) was added at 80° C. 5-(2-(2-fluoroethoxy)ethoxy)-2-methylpyridine 1-oxide (562 mg, 1.645 mmol). The reaction mixture was heated up to 130° C. and stirred for 30 min. The resulting mixture was poured into ice water and then stirred at RT for 15 min. The product was extracted with EtOAc. The organic layer was washed with sat. aq. NaHCO$_3$ and brine. The aqueous layer was extracted with EtOAc. The combined organic layers were dried over a phase separator and concentrated to give the crude product as a brown oil which was purified by flash chromatography (cyclohexane/EtOAc, 100:0 to 60/40) to afford 352 mg of title compound as yellow oil.

LC MS: Rt 0.71 min; [M+H]$^+$258.1; 2 min Final Analysis

Step 6: (5-(2-(2-fluoroethoxy)ethoxy)pyridin-2-yl) methanol

To a solution of (5-(2-(2-fluoroethoxy)ethoxy)pyridin-2-yl)methyl acetate (352 mg, 1.08 mmol) in EtOH (4.7 mL) and water (0.82 mL) was added NaOH (86 mg, 2.16 mmol). The resulting reaction mixture was stirred at reflux for 1 h. The solvents were evaporated and the residue was extracted twice with EtOAc. The combined organic layers were dried over a phase separator and concentrated to give 282 mg of crude product as orange oil.

LC MS: Rt 0.43 min; [M+H]$^+$216.1; 2 min Final Analysis

Step 7: 5-(2-(2-fluoroethoxy)ethoxy)picolinaldehyde

To a solution of (5-(2-(2-fluoroethoxy)ethoxy)pyridin-2-yl)methanol (282 mg, 1.05 mmol) in CH$_2$Cl$_2$ (4.0 mL) was added MnO$_2$ (911 mg, 10.5 mmol). The resulting reaction mixture was stirred at RT for 2 days. The reaction mixture was filtered over Celite and washed three times with EtOAc. The filtrate was evaporated to dryness to give 185 mg of crude product as yellow oil.

LC MS: Rt 0.65 min; [M+H]$^+$214.0; 2 min Final Analysis

Intermediate D 2-(fluoromethyl)oxazole-4-carbaldehyde

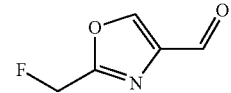

Step 1: Methyl 2-(fluoromethyl)oxazole-4-carboxylate

To a solution of methyl 2-(chloromethyl)oxazole-4-carboxylate (1.0 g, 5.70 mmol) in CH$_3$CN (28.5 mL) was added TBAF (1M in THF) (17.09 mL, 17.09 mmol) at RT. The resulting green solution was stirred for 21 h under argon at RT. The reaction mixture was poured in water and extracted twice with EtOAc. The combined organic layers were washed with brine, dried over a Phase Separator and concentrated to give crude product as orange oil. The crude product was purified by preparative HPLC (Waters SunFire C18ODB, 5 µm, 30×100, eluent: 1% MeCN/99% H$_2$O to 30% MeCN/70% H₂O in 20 min, H₂O contains 0.1% of TFA, flow 40 mL/min). The fractions containing the desired product were combined, diluted with EtOAc and washed with sat. aq. NaHCO₃. The aqueous layer was extracted with EtOAc. The combined organic layers were washed with brine, dried over a phase separator and concentrated to give 291 mg of a white solid.

¹H NMR (400 MHz, DMSO-d6) δ ppm 3.76 (s, 3H) 5.43 (s, 1H) 5.55 (s, 1H) 8.91 (d, J=1.34 Hz, 1H)

LC MS Rt 0.49 min; [M+H]⁺160.0; 2 min Final Analysis

Step 2: (2-(fluoromethyl)oxazol-4-yl)methanol

To a solution of methyl 2-(fluoromethyl)oxazole-4-carboxylate (291 mg, 1.46 mmol) in THF (3.6 mL) at −78° C. under argon, was added dropwise DIBAL-H (1M in THF) (3.22 mL, 3.22 mmol). The reaction mixture was then stirred at −78° C. for 3 h and at RT for 16 h. UPLC/MS showed remaining starting material therefore the reaction mixture was cooled down to −78° C. and DIBAL-H (1M in THF) (3.22 mL, 3.22 mmol) was added stirred at −78° C. for 3 h. The resulting mixture was diluted with CH₂Cl₂ at −78° C., then quenched with MeOH/water/2M aq. NaOH and stirred for 15 min. Na₂SO₄ was added at RT and the suspension stirred for 15 min. The salts were removed by filtration and the filtrate was concentrated under vacuum. The crude product was purified by flash chromatography (CH₂Cl₂/MeOH: from 100/0 to 95/5) to afford the title compound as yellow oil (79 mg).

¹H NMR (400 MHz, DMSO-d6) δ ppm 4.31-4.34 (m, 2H) 5.32 (s, 1H) 5.44 (s, 1H) 7.84-8.03 (m, 1H)

LC MS Rt 0.32 min; [M+H]⁺132.0; 2 min Final Analysis

Step 3: 2-(fluoromethyl)oxazole-4-carbaldehyde

To a solution of (2-(fluoromethyl)oxazol-4-yl)methanol (78 mg, 0.6 mmol) in CH₂Cl₂ (6 mL) was added MnO₂ (517 mg, 5.95 mmol). The resulting mixture was stirred at RT for 2 days. The reaction mixture was filtered over Celite and washed three times with CH₂Cl₂. The filtrate was evaporated to dryness to give 32 mg of crude product. The crude product was used in the next step without further purification.

LC MS Rt 0.34 min; [M+H]⁺130.0; 2 min Final Analysis

Preparation of the Examples

Example 1

(R,E)-3-(4-chloro-2-((5-methyl-2H-tetrazol-2-yl)methyl)phenyl)-1-(4-((5-(2-fluoroethoxy)pyridin-2-yl)methyl)-2-methylpiperazin-1-yl)prop-2-en-1-one Step 1: (R,E)-3-(4-chloro-2-((5-methyl-2H-tetrazol-2-yl)methyl)phenyl)-1-(4-((5-hydroxypyridin-2-yl)methyl)-2-methylpiperazin-1-yl)prop-2-en-1-one A stirred solution of (R,E)-3-(4-chloro-2-((5-methyl-2H-tetrazol-2-yl)methyl)phenyl)-1-(2-methylpiperazin-1-yl)prop-2-en-1-one (intermediate A) (3.0 g, 8.3 mmol) in DCE (60 mL) was treated with 5-hydroxypyridine-2-carboxaldehyde (2.0 g, 16.6 mmol), sodium triacetoxyborohydride (3.5 g, 16.62 mmol) and acetic acid (0.95 mL) at 0° C. The resulting mixture was stirred at RT for 17 h. The solvent was evaporated, water was added to the residue, and the aqueous phase was extracted with EtOAc. The organic layer was washed with sat. aq. NaHCO₃, brine, dried over Na₂SO₄, filtered and concentrated under vacuum. The residue was purified by flash chromatography on silica gel.

HLPC Rt: 5.7 min (analytical HPLC)

Step 2: (R,E)-3-(4-chloro-2-((5-methyl-2H-tetrazol-2-yl)methyl)phenyl)-1-(4-((5-(2-fluoroethoxy)pyridin-2-yl)methyl)-2-methylpiperazin-1-yl)prop-2-en-1-one To a solution of (R,E)-3-(4-chloro-2-((5-methyl-2H-tetrazol-2-yl)methyl)phenyl)-1-(4-((5-hydroxypyridin-2-yl)methyl)-2-methylpiperazin-1-yl)prop-2-en-1-one (1.5 g, 3.2 mmol) in DMF (15 mL) was added Cs₂CO₃ (1.53 g, 4.8 mmol) followed by 1-bromo-2-fluoroethane (488 mg, 3.8 mmol) under N₂. The reaction mixture was stirred at RT for 16 h. The reaction mixture was diluted with water and the aqueous solution was extracted with ethyl acetate. The combined organic solutions were dried over sodium sulfate, filtered and concentrated in vacuo. The crude product was purified by preparative HPLC.

¹H NMR (400 MHz, DMSO-d6, 100° C.) δ ppm 1.26-1.31 (m, 4H) 2.09 (d, J=3.26 Hz, 1H) 2.24 (dd, J=11.36, 3.83 Hz, 1H) 2.44 (s, 3H) 2.72 (d, J=11.29 Hz, 1H) 2.82-2.90 (m, 1H) 3.10-3.24 (m, 1H) 3.52-3.65 (m, 2H) 4.02-4.17 (m, 1H) 4.29-4.34 (m, 1H) 4.36-4.42 (m, 1H) 4.46-4.58 (m, 1H) 4.66-4.74 (m, 1H) 4.78-4.86 (m, 1H) 5.96 (s, 2H) 7.03 (d, J=15.43 Hz, 1H) 7.42 (d, J=1.76 Hz, 2H) 7.44-7.51 (m, 2H) 7.71 (d, J=15.31 Hz, 1H) 7.81 (d, J=8.41 Hz, 1H) 8.26 (t, J=1.76 Hz, 1H)

LC MS: Rt 0.87 min; [M+H]+514.1; 2 min Final Analysis

Example 2

(R,E)-1-(4-((5-(2-fluoroethoxy)pyridin-2-yl)methyl)-2-methylpiperazin-1-yl)-3-(2-((5-methyl-2H-tetrazol-2-yl)methyl)-4-(trifluoromethyl)phenyl)prop-2-en-1-one

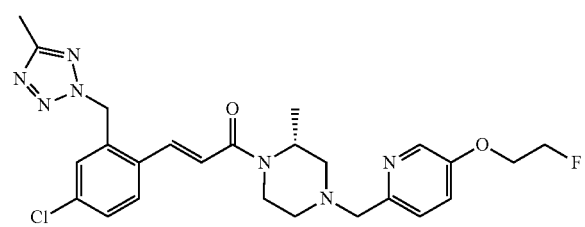 [SMILES: Cc1nnn(Cc2cc(Cl)ccc2/C=C/C(=O)N2CCN(Cc3ccc(OCCF)cn3)C[C@H]2C)n1]

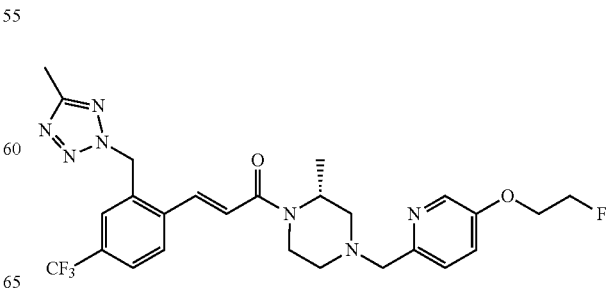

The title compound was prepared by a similar method to Example 1, but from (R,E)-3-(2-((5-methyl-2H-tetrazol-2-yl)methyl)-4-(trifluoromethyl)phenyl)-1-(2-methylpiperazin-1-yl)prop-2-en-1-one (intermediate B).

¹H NMR (400 MHz, DMSO-d6, 100° C.) δ ppm 1.29 (d, J=6.78 Hz, 3H) 2.00-2.14 (m, 1H) 2.21-2.29 (m, 1H) 2.44 (s, 3H) 2.66-2.76 (m, 1H) 2.84-2.92 (m, 1H) 3.12-3.25 (m, 1H) 3.60 (d, J=10.67 Hz, 2H) 4.06-4.17 (m, 1H) 4.28-4.34 (m, 1H) 4.35-4.42 (m, 1H) 4.45-4.58 (m, 1H) 4.66-4.74 (m, 1H) 4.78-4.87 (m, 1H) 6.06 (s, 2H) 7.11 (d, J=15.43 Hz, 1H) 7.42 (d, J=1.88 Hz, 2H) 7.77 (d, J=5.65 Hz, 3H) 7.92-8.04 (m, 1H) 8.26 (s, 1H)

LC MS: Rt 0.92 min; [M+H]+548.0; 2 min Final Analysis saturated solution of NaHCO₃. The aqueous layer was extracted with EtOAc and the combined organic layers were washed with brine, dried over a phase separator, concentrated and dried under vacuum to give the title compound (22 mg, 47%).

¹H NMR (400 MHz, DMSO-d6) δ ppm 1.16-1.22 (m, 3H) 1.27-1.31 (m, 1H) 1.92-2.13 (m, 2H) 2.46 (s, 3H) 2.55-2.85 (m, 4H) 3.04-3.07 (m, 3H) 3.48-3.62 (m, 2H) 3.78-4.03 (m, 1H) 4.28-4.41 (m, 2H) 4.66-4.85 (m, 2H) 5.96-6.08 (m, 2H) 7.35-7.44 (m, 2H) 7.53-7.71 (m, 3H) 8.21-8.29 (m, 1H)

LC MS: Rt 0.89 min; [M+H]+550.1; 2 min Final Analysis

Example 4

(R,E)-3-(4-chloro-2-((5-methyl-2H-tetrazol-2-yl)methyl)phenyl)-1-(4-((5-(2-(2-fluoroethoxy)ethoxy)pyridin-2-yl)methyl)-2-methylpiperazin-1-yl)prop-2-en-1-one

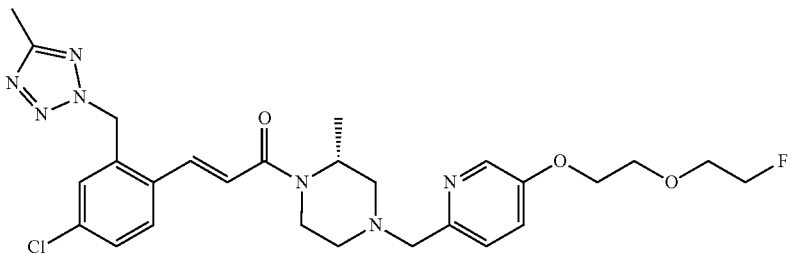

Example 3

(R)-1-(4-((5-(2-fluoroethoxy)pyridin-2-yl)methyl)-2-methylpiperazin-1-yl)-3-(2-((5-methyl-2H-tetrazol-2-yl)methyl)-4-(trifluoromethyl)phenyl)propan-1-one

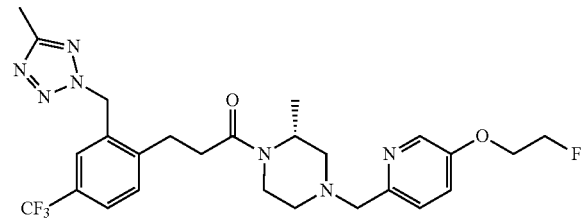 [SMILES: Cc1nnn(Cc2cc(C(F)(F)F)ccc2CCC(=O)N2CCN(Cc3ccc(OCCF)cn3)C[C@H]2C)n1]

A solution of (R,E)-1-(4-((5-(2-fluoroethoxy)pyridin-2-yl)methyl)-2-methylpiperazin-1-yl)-3-(2-((5-methyl-2H-tetrazol-2-yl)methyl)-4-(trifluoromethyl)phenyl)prop-2-en-1-one (46 mg, 0.084 mmol) and Pd/C (10%) (5.72 mg, 5.38 μmol) in EtOH (4.00 mL) was stirred at RT under hydrogen for 18 h. The reaction mixture was filtered over Celite and concentrated. The residue was taken up in 1 mL of MeOH and purified by preparative HPLC (Waters SunFire C18ODB, 5 μm, 30×100, eluent: 5% MeCN/95% H₂O to 50% MeCN/50% H₂O in 20 min, H₂O contains 0.1% of TFA, flow 40 mL/min). The fractions containing the product were combined and lyophilized overnight. The resulting white powder was diluted with EtOAc and washed with a To (R,E)-3-(4-chloro-2-((5-methyl-2H-tetrazol-2-yl)methyl)phenyl)-1-(2-methylpiperazin-1-yl)prop-2-en-1-one (intermediate A) (80 mg, 0.22 mmol) in MeOH (2.0 mL) were added AcOH (0.2 mL) and 5-(2-(2-fluoroethoxy)ethoxy)picolinaldehyde (intermediate C) (93 mg, 0.33 mmol). After stirring for 5 min, 2-picoline borane (44.2 mg, 0.35 mmol) was added. The reaction mixture was stirred at RT for 20 h. The volatiles were evaporated and the residue purified by preparative HPLC (Waters SunFire C18ODB, 5 μm, 30×100, eluent: 5% MeCN/95% H₂O to 50% MeCN/50% H₂O in 20 min, H₂O contains 0.1% of TFA, flow 40 mL/min). The desired fractions were concentrated. The residue was taken up in EtOAc and washed with a saturated solution of NaHCO₃. The aqueous layer was extracted with EtOAc. The combined organic layers were washed with brine, dried over a phase separator and concentrated to give 63 mg yellow oil.

¹H NMR (400 MHz, DMSO-d6, 100° C.) δ ppm 1.28 (d, J=6.78 Hz, 3H) 2.01-2.15 (m, 1H) 2.25 (dd, J=11.48, 3.07 Hz, 1H) 2.44 (s, 3H) 2.73 (d, J=11.42 Hz, 1H) 2.88 (d, J=11.29 Hz, 1H) 3.17 (br. s., 1H) 3.52-3.66 (m, 2H) 3.70-3.76 (m, 1H) 3.78-3.88 (m, 3H) 4.12 (d, J=12.55 Hz, 1H) 4.18-4.28 (m, 2H) 4.44-4.56 (m, 2H) 4.57-4.65 (m, 1H) 5.96 (s, 2H) 7.03 (d, J=15.31 Hz, 1H) 7.40 (d, J=1.76 Hz, 2H) 7.44-7.51 (m, 2H) 7.71 (d, J=15.31 Hz, 1H) 7.81 (d, J=8.41 Hz, 1H) 8.24 (t, J=1.69 Hz, 1H)

LC MS Rt 0.87 min; [M]+558.2, 560.1; 2 min Final Analysis

Example 5

(R,E)-1-(4-((5-(2-(2-fluoroethoxy)ethoxy)pyridin-2-yl)methyl)-2-methylpiperazin-1-yl)-3-(2-((5-methyl-2H-tetrazol-2-yl)methyl)-4-(trifluoromethyl)phenyl) prop-2-en-1-one

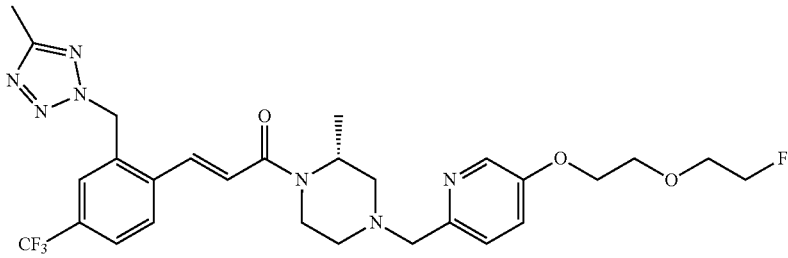 [SMILES: Cc1nnn(Cc2cc(C(F)(F)F)ccc2/C=C/C(=O)N2CCN(Cc3ccc(OCCOCCF)cn3)C[C@H]2C)n1]

The title compound was prepared by a similar method to Example 4, from (R,E)-3-(2-((5-methyl-2H-tetrazol-2-yl)methyl)-4-(trifluoromethyl)phenyl)-1-(2-methylpiperazin-1-yl)prop-2-en-1-one (intermediate B) and 5-(2-(2-fluoroethoxy)ethoxy)picolinaldehyde (intermediate C).

$^1$H NMR (400 MHz, DMSO-d6) δ ppm 1.29 (d, J=6.65 Hz, 3H) 2.09 (td, J=11.67, 3.14 Hz, 1H) 2.24 (dd, J=11.36, 3.70 Hz, 1H) 2.40-2.46 (m, 3H) 2.72 (d, J=11.29 Hz, 1H) 2.88 (d, J=11.17 Hz, 1H) 3.12-3.27 (m, 1H) 3.50-3.64 (m, 2H) 3.70-3.75 (m, 1H) 3.78-3.87 (m, 3H) 4.12 (d, J=13.80 Hz, 1H) 4.19-4.26 (m, 2H) 4.43-4.54 (m, 2H) 4.57-4.65 (m, 1H) 6.06 (s, 2H) 7.11 (d, J=15.43 Hz, 1H) 7.40 (d, J=1.13 Hz, 2H) 7.69-7.84 (m, 3H) 7.99 (d, J=8.53 Hz, 1H) 8.24 (s, 1H)

LC MS Rt 0.92 min; [M+H]$^+$592.2; 2 min Final Analysis

Example 6

(R,E)-1-(4-((2-(fluoromethyl)oxazol-4-yl)methyl)-2-methylpiperazin-1-yl)-3-(2-((5-methyl-2H-tetrazol-2-yl)methyl)-4-(trifluoromethyl)phenyl)prop-2-en-1-one

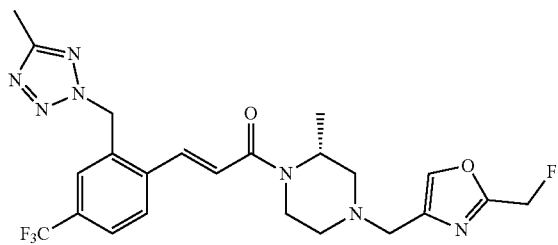 [SMILES: Cc1nnn(Cc2cc(C(F)(F)F)ccc2/C=C/C(=O)N2CCN(Cc3coc(CF)n3)C[C@H]2C)n1]

The title compound was prepared by a similar method to Example 4, from (R,E)-3-(2-((5-methyl-2H-tetrazol-2-yl)methyl)-4-(trifluoromethyl)phenyl)-1-(2-methylpiperazin-1-yl)prop-2-en-1-one (intermediate B) and 2-(fluoromethyl)oxazole-4-carbaldehyde (intermediate D).

$^1$H NMR (400 MHz, DMSO-d6) δ ppm 1.27 (d, J=6.97 Hz, 3H) 2.05-2.11 (m, 1H) 2.23-2.27 (m, 1H) 2.44 (s, 3H) 2.76-2.80 (m, 1H) 2.90-2.95 (m, 1H) 3.10-3.20 (m, 1H) 3.5 (s, 2H) 4.1 (d, 1H) 4.5 (s, 1H) 4.45 (d, 2H) 6.06 (s, 2H) 7.1 (d, 1H) 7.70-7.80 (m, 4H) 7.98-8.01 (m, 1H)

LC MS Rt 0.89 min; [M+H]$^+$508.3; 2 min Final Analysis

Example 7: (R,E)-3-(4-chloro-2-((5-methyl-2H-tetrazol-2-yl)methyl)phenyl)-1-(4-((5-(2-[$^{18}$F]fluoroethoxy)pyridin-2-yl)methyl)-2-methylpiperazin-1-yl)prop-2-en-1-one

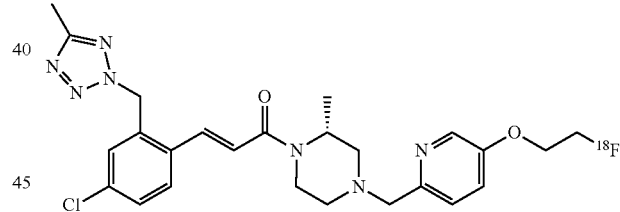

Step 1: Synthesis of (R,E)-2-((6-((4-(3-(4-chloro-2-((5-methyl-2H-tetrazol-2-yl)methyl)phenyl)acryloyl)-3-methylpiperazin-1-yl)methyl)pyridin-3-yl)oxy)ethyl 4-methylbenzenesulfonate

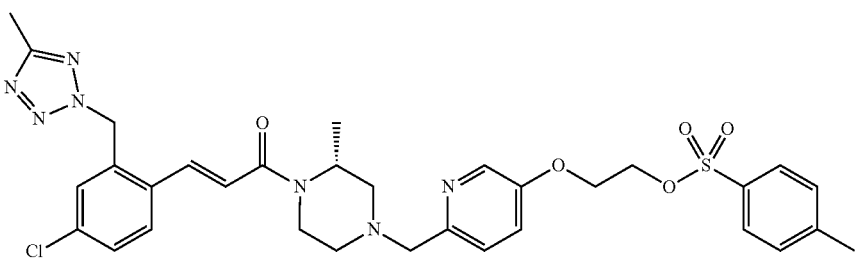 [SMILES: Cc1ccc(S(=O)(=O)OCCOc2ccc(CN3CCN(C(=O)/C=C/c4ccc(Cl)cc4Cn4nnc(C)n4)[C@H](C)C3)nc2)cc1]

Cs$_2$CO$_3$ (446 mg, 1.37 mmol) was added to a solution of ethylene di(p-toluenesulfonate) (475 mg, 1.28 mmol) in DMF (20 mL) under argon at RT, followed by the addition of (R,E)-3-(4-chloro-2-((5-methyl-2H-tetrazol-2-yl)methyl) phenyl)-1-(4-((5-hydroxypyridin-2-yl)methyl)-2-methyl-piperazin-1-yl)prop-2-en-1-one (200 mg, 0.43 mmol) in DMF (20 mL) over a period of 1 h. The reaction mixture was stirred at RT for 2 h. The reaction mixture was diluted with water and the aqueous solution was extracted with ethyl acetate. The combined organic solutions were dried (Phase Separator) and concentrated. The crude product was purified by flash chromatography on silica gel (cyclohexane/EtOAc 100:0 to 0:100) to obtain the desired product as a colorless oil (180 mg, 62%). $^1$H NMR (400 MHz, 300° C., DMSO-d6) δ ppm 1.12-1.27 (m, 3H), 1.97 (s, 1H), 2.11 (s, 1H), 2.40 (d, J=4.0 Hz, 6H), 2.64 (d, J=11.3 Hz, 1H) 2.80 (d, J=11.0 Hz, 1H), 3.27 (s, 1H), 3.44-3.59 (m, 2H), 4.01 (q, J=7.1 Hz, 1H), 4.22 (dd, J=5.3, 2.8 Hz, 2H), 4.34 (dd, J=5.3, 2.8 Hz, 2H), 4.4 (s, 1H), 6.03-5.91 (m, 2H), 7.11 (d, J=15.2 Hz, 1H), 7.29 (dd, J=8.6, 2.9 Hz, 1H), 7.35 (d, J=8.6 Hz, 1H), 7.43-7.51 (m, 4H), 7.70 (d, J=15.2 Hz, 1H), 7.78 (d, J=8.3 Hz, 2H), 7.87 (d, J=9.1 Hz, 1H), 8.07 (d, J=2.8 Hz, 1H); LC MS: Rt 1.06 min; [M]+666.5; Method: 2 min Final Analysis.

Step 2: Synthesis of Example 7

(R,E)-3-(4-chloro-2-((5-methyl-2H-tetrazol-2-yl) methyl)phenyl)-1-(4-((5-(2-[$^{18}$F]fluoroethoxy)pyridin-2-yl)methyl)-2-methylpiperazin-1-yl)prop-2-en-1-one

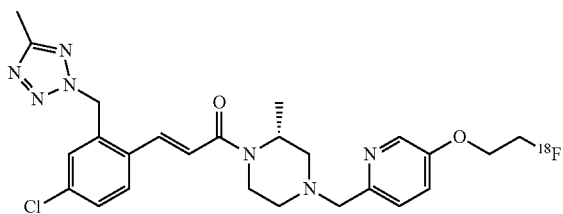 [SMILES: Cc1nnn(Cc2cc(Cl)ccc2/C=C/C(=O)N2CCN(Cc3ccc(OCC[18F])cn3)C[C@H]2C)n1]

In a sealed reaction vial, [$^{18}$F]KF/Kryptofix 222 in anhydrous DMSO was added to (R,E)-2-((6-((4-(3-(4-chloro-2-((5-methyl-2H-tetrazol-2-yl)methyl)phenyl)acryloyl)-3-methylpiperazin-1-yl)methyl)pyridin-3-yl)oxy)ethyl 4-methylbenzenesulfonate and heated for 10 minutes at 140° C. The labelled product was purified by semi-preparative HPLC (Phenomenex Luna C18(2), 250×10 mm; eluent: CH$_3$CN/H$_2$O/NEt$_3$ (50/50/0.1); flow: 4 mL/min). The analysis by HPLC (Waters XBridge C18, 150×4.6 mm; MeOH/H$_2$O/NEt$_3$ (70/30/0.08), 1 mL/min) gave a retention time of 6.37 minutes. The comparison with a cold reference HPLC trace (6.28 minutes) confirmed the product to be example 7, which was obtained with a decay-corrected radiochemical yield of 8%.

Example 8: (E)-3-(4-chloro-2-((5-methyl-2H-tetrazol-2-yl)methyl)phenyl)-1-((2R)-4-((5-(2-fluoroethoxy-1,2-t2)pyridin-2-yl)methyl)-2-methylpiperazin-1-yl)prop-2-en-1-one

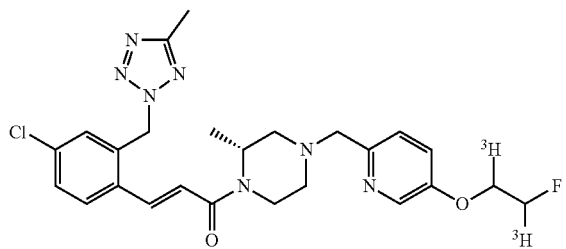 [SMILES: [3H]C(F)C([3H])Oc1ccc(CN2CCN(C(=O)/C=C/c3ccc(Cl)cc3Cn3nnc(C)n3)[C@H](C)C2)nc1]

Step 1: Synthesis of [$^3$H]$_2$-2-fluoroethyl 4-(p-tolyl) benzenesulfonate 6.15 mg (21.0 μmol) of (E)-2-fluorovinyl 4'-methyl-[1,1'-biphenyl]-4-sulfonate and 7.07 mg (8.78 μmol; 0.42 eq.) of Crabtree's catalyst (Strem 77-9500) were dissolved in 0.75 mL dichloromethane (Fluka 66740). The deep orange solution was degassed three times at the high vacuum manifold and stirred under an atmosphere of tritium gas (8.7 Ci) for 3.5 h at room temperature. The initial pressure when the solvent was still frozen was 347 mbar, while the maximum pressure at room temperature was 962 mbar. The solvent was removed in vacuo, and labile tritium was exchanged by adding 1 mL of methanol (Fluka 65543), stirring the solution, and removing the solvent again under vacuo. This process was repeated three times. Finally, the dried solid was extracted with 5 mL of THF. The activity of the crude product was 1003 mCi (37.1 GBq). The radiochemical purity (RCP) was determined to be 74% using the following HPLC system: Macherey+Nagel Nucleodur Gravity C18 (5 μm, 4.6×150 mm); solvents: A, 10 mM aq. NH$_4$OAc; B, MeCN; gradient: 0 min 40% B; 10 min 100% B; 14.5 min 100% B; 15 min 40% B; detection at 254 nm; flow rate 1.0 ml/min; 30° C. The crude product was used for the next step without further purification.

Synthesis of Example 8

100 mCi (3.7 GBq) of crude [$^3$H]$_2$-2-fluoroethyl 4-(p-tolyl)benzenesulfonate (0.5 ml, 2.1 μmol) were evaporated to dryness and a solution of 3.04 mg (6.5 mol; 3.1 eq.) of (R,E)-3-(4-chloro-2-((5-methyl-2H-tetrazol-2-yl)methyl)phenyl)-1-(4-((5-hydroxypyridin-2-yl)methyl)-2-methyl-piperazin-1-yl)prop-2-en-1-one in 0.25 ml DMF was added. Then the solution was treated with 4.36 mg (13.4 mol; 6.4 eq.) of cesium carbonate and stirred in a water bath at 50° C. for 2.2 h. A reaction control by HPLC (conditions as above) showed a quantitative conversion of the labelled starting material and the RCP was determined to 63%. The reaction mixture was purified by HPLC using the following conditions: Macherey+Nagel Nucleodur Gravity C18, 5 μm, 8×150 mm; solvents: A, 10 mM NH$_4$OAc; B, MeCN; gradient: 0 min 48.5% B; 8 min 48.5% B; 8.5 min 95% B; 12.5 min 95% B; 13 min 48.5% B.; detection at 254 nm and 230 nm; flow rate: 3.1 ml/min; 20° C. The desired compound eluted after 6.7 min.

The desired product was isolated from the HPLC solvent mixture by solid phase extraction. The volume of the fractions was partially reduced at the rotary evaporator and the product was extracted with a Phenomenex StrataX cartridge (3 mL, 100 mg) which was eluted with 10 mL of ethanol. The extracted product with an activity of 40.5 mCi (1.50 GBq) showed a RCP of >99%. The specific activity was determined to 38.5 Ci/mmol (1.43 TBq/mmol). The comparison with a cold reference HPLC trace confirmed the identity of the product. HPLC conditions: Macherey+Nagel Nucleodur Gravity C18, 4.6×150 mm (5 μm); mobile phase: A, 10 mM NH$_4$OAc; B: MeCN; gradient: 0 min 35% B; 10 min 95% B; 14.5 min 95% B; 15 min 35% B; flow rate 1.0 mL/min. Reference retention time (UV detection): 7.14 min; Product retention time (radioactivity detection): 7.25 min. The delay between UV and radio signal is due to the serial detection system.

1) (R,E)-3-(4-chloro-2-((5-methyl-2H-tetrazol-2-yl)methyl)phenyl)-1-(4-((5-(2-(2-[$^{18}$F]fluoroethoxy)ethoxy)pyridin-2-yl)methyl)-2-methylpiperazin-1-yl)prop-2-en-1-one

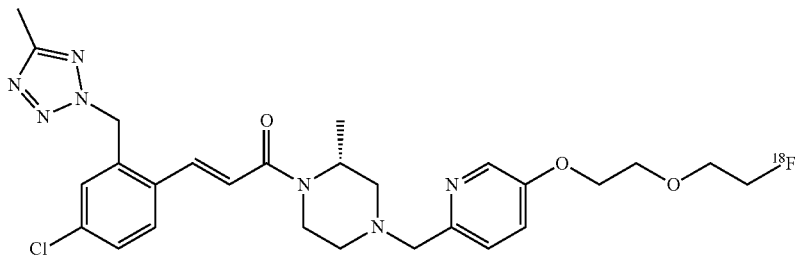 [SMILES: Cc1nnn(Cc2cc(Cl)ccc2/C=C/C(=O)N2CCN(Cc3ccc(OCCOCC[18F])cn3)C[C@H]2C)n1]

The precursor (R,E)-2-(2-((6-((4-(3-(4-chloro-2-((5-methyl-2H-tetrazol-2-yl)methyl)phenyl)acryloyl)-3-methylpiperazin-1-yl)methyl)pyridin-3-yl)oxy)ethoxy)ethyl 4-methylbenzenesulfonate may be prepared by a similar method to compound 4 from (R,E)-3-(4-chloro-2-((5-methyl-2H-tetrazol-2-yl)methyl)phenyl)-1-(2-methylpiperazin-1-yl)prop-2-en-1-one (intermediate A) and 2-(2-((6-formylpyridin-3-yl)oxy)ethoxy)ethyl 4-methylbenzenesulfonate.

The synthesis of (R,E)-3-(4-chloro-2-((5-methyl-2H-tetrazol-2-yl)methyl)phenyl)-1-(4-((5-(2-(2-[$^{18}$F]fluoroethoxy)ethoxy)pyridin-2-yl)methyl)-2-methylpiperazin-1-yl)prop-2-en-1-one may be performed by treating (R,E)-2-(2-((6-((4-(3-(4-chloro-2-((5-methyl-2H-tetrazol-2-yl)methyl)phenypacryloyl)-3-methylpiperazin-1-yl)methyl)pyridin-3-yl)oxy)ethoxy)ethyl 4-methylbenzene sulfonate with [$^{18}$F]KF/K222 or [$^{18}$F]TBAF in a polar nonprotic solvent such as DMF, DMSO or CH$_3$CN.

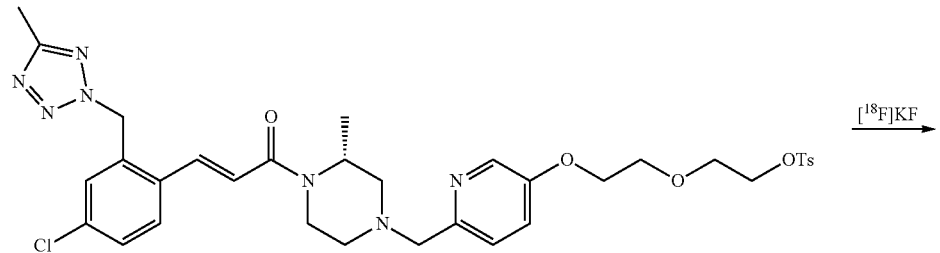

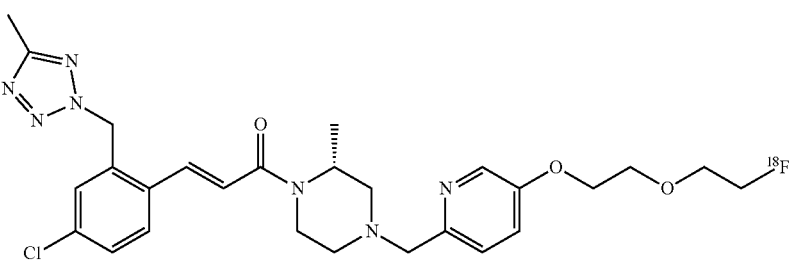

2) Synthesis of (R,E)-3-(4-chloro-2-((5-methyl-2H-tetrazol-2-yl)methyl)phenyl)-1-(4-((5-(2-fluoroethoxy)pyridin-2-yl)methyl)-2-methylpiperazin-1-yl)[carbonyl-¹¹C]prop-2-en-1-one

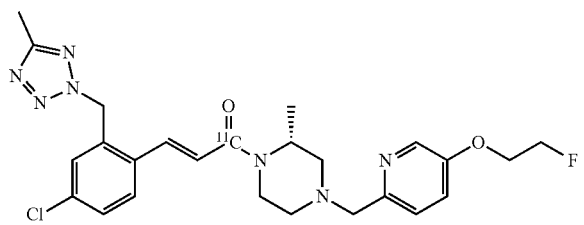 [SMILES: Cc1nnn(Cc2cc(Cl)ccc2/C=C/[11C](=O)N2CCN(Cc3ccc(OCCF)cn3)C[C@H]2C)n1]

In a first step, the precursor for radiolabeling may be prepared as shown below:

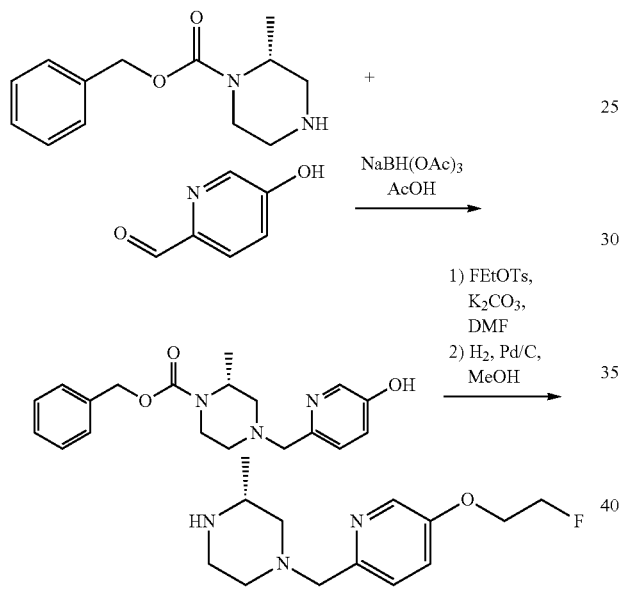

The reductive amination of 5-hydroxypicolinaldehyde with (R)-benzyl 2-methylpiperazine-1-carboxylate using sodium triacetoxyborohydride and acetic acid may provide (R)-benzyl 4-((5-hydroxypyridin-2-yl)methyl)-2-methylpiperazine-1-carboxylate. This intermediate may further react with 2-fluoroethyl-tosylate in the presence of a base such as potassium carbonate followed by hydrogenation using palladium over carbon and hydrogen gas to lead to (R)-1-((5-(2-fluoroethoxy)pyridin-2-yl)methyl)-3-methyl-piperazine.

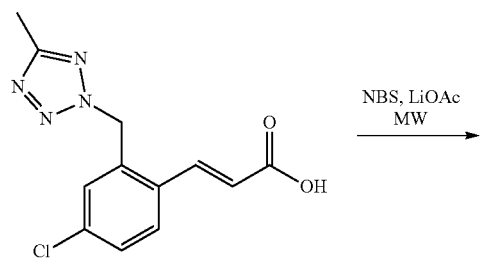

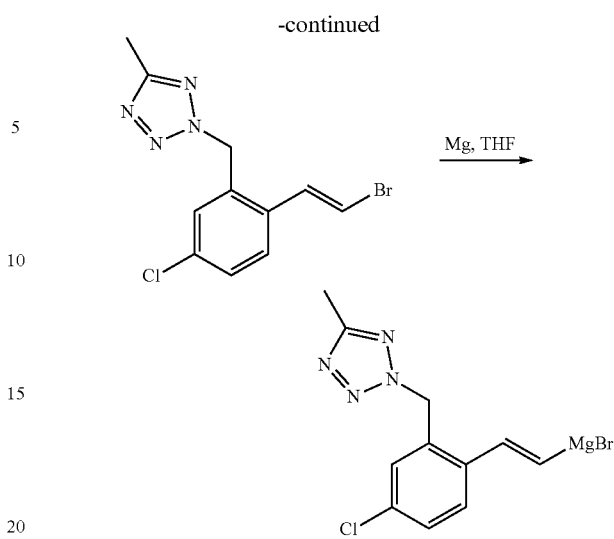

(E)-2-(2-(2-bromovinyl)-5-chlorobenzyl)-5-methyl-2H-tetrazole may be prepared by microwave irradiation of (E)-3-(4-chloro-2-((5-methyl-2H-tetrazol-2-yl)methyl)phenyl)acrylic acid in the presence of N-bromosuccinimide and a catalytic amount of lithium acetate. The resulting arylvinyl bromide may be converted into (E)-(4-chloro-2-((5-methyl-2H-tetrazol-2-yl)methyl)styryl)magnesium bromide using magnesium in THF.

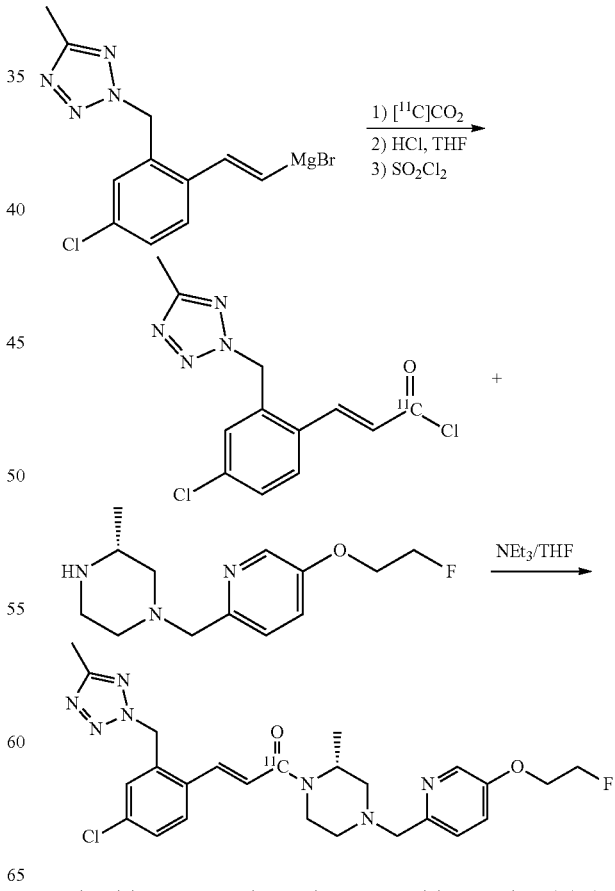

The title compound may be prepared by treating (E)-(4-chloro-2-((5-methyl-2H-tetrazol-2-yl)methyl)styryl)magnesium bromide with [$^{11}$C]CO$_2$ to form the [$^{11}$C]carboxymagnesium halide and then transformed into the [$^{11}$C]carboxylic acid. This could then be converted into an acid chloride and treated with (R)-1-((5-(2-fluoroethoxy)pyridin-2-yl)methyl)-3-methylpiperazine to afford the desired amide.

3) (R)-1-(4-((5-(2-fluoroethoxy)pyridin-2-yl)methyl)-2-methylpiperazin-1-yl)-3-(2-((5-methyl-2H-tetrazol-2-yl)methyl)-4-[$^{18}$F](trifluoromethyl)phenyl) prop-2-en-1-one

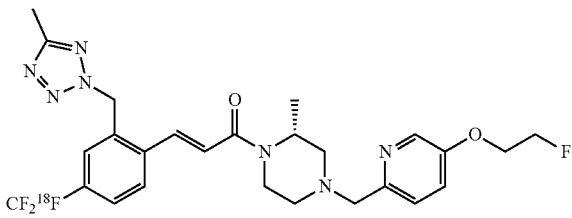

The precursor (R,E)-1-(4-((5-(2-fluoroethoxy)pyridin-2-yl)methyl)-2-methylpiperazin-1-yl)-3-(4-iodo-2-((5-methyl-2H-tetrazol-2-yl)methyl)phenyl)prop-2-en-1-one may be obtained by following a similar protocol to example 1, starting from 5-methyl-2H-tetrazole and 1-bromo-2-(bromomethyl)-4-iodobenzene.

4) Synthesis of (R,E)-3-(4-chloro-2-((5-methyl-2H-tetrazol-2-yl)methyl)phenyl)-1-(4-((5-(2-fluoro[$^3$H$_2$]ethoxy)pyridin-2-yl)methyl)-2-methylpiperazin-1-yl) prop-2-en-1-one

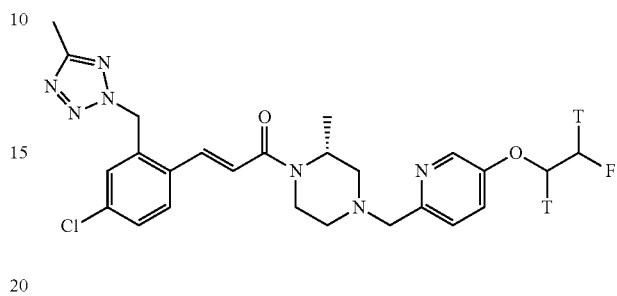

The synthesis of [$^3$H]2-fluoroethyl-4-methylbenzenesulfonate was reported by Cochrane et al (Journal of Labelled Compounds, 2013, 56, 447-((50). The title compound may be obtained by treating (R,E)-3-(4-chloro-2-((5-methyl-2H-tetrazol-2-yl)methyl)phenyl)-1-(4-((5-hydroxypyridin-2-yl)methyl)-2-methylpipe razin-1-yl)prop-2-en-1-one with [$^3$H]2-fluoroethyl-4-methylbenzenesulfonate in the presence of a base such as cesium carbonate.

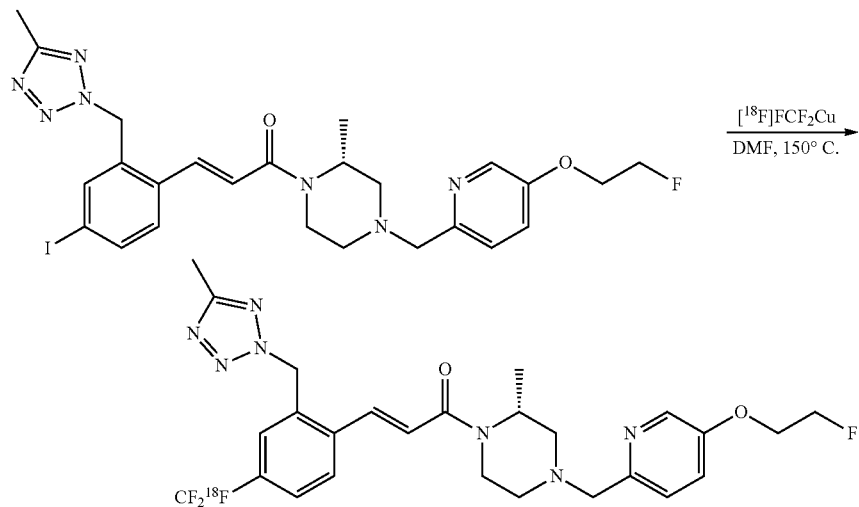

Following the protocol reported by Huiban et al (Nature Chemistry, 2013) for the late-stage [$^{18}$F]trifluoromethylation of (hetero)arenes from [$^{18}$F]fluoride, this example depicts a possible synthetic route to generate (R)-1-(4-((5-(2-fluoroethoxy)pyridin-2-yl)methyl)-2-methylpiperazin-1-yl)-3-(2-((5-methyl-2H-tetrazol-2-yl)methyl)-4-[$^{18}$F](trifluoromethyl)phenyl) prop-2-en-1-one. [$^{18}$F]CF$_3$Cu may be generated in situ from methyl chlorodifluoroacetate, CuI, TMEDA and [$^{18}$F]fluoride may react with (R,E)-1-(4-((5-(2-fluoroethoxy)pyridin-2-yl)methyl)-2-methylpiperazin-1-yl)-3-(4-iodo-2-((5-methyl-2H-tetrazol-2-yl)methyl)phenyl) prop-2-en-1-one to provide the title compound.

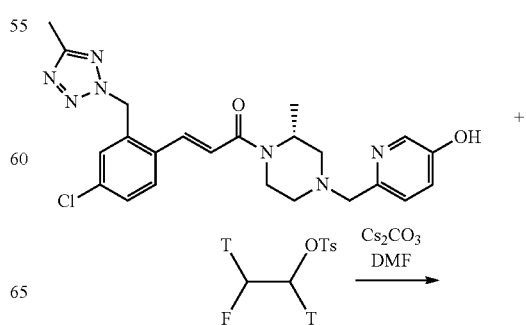

-continued

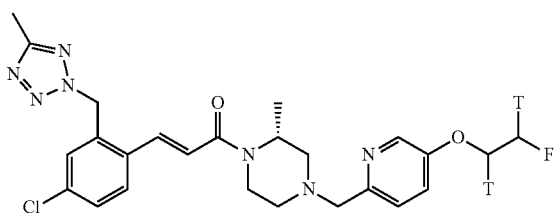

5) Synthesis of [¹¹C]CN-containing examples, e.g. (R,E)-4-(3-(4-((5-(2-fluoroethoxy)pyridin-2-yl)methyl)-2-methylpiperazin-1-yl)-3-oxoprop-1-en-1-yl)-3-((5-methyl-2H-tetrazol-2-yl)methyl)benzonitrile

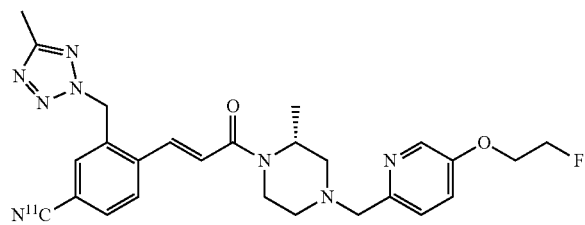

The [¹¹C]CN group may be introduced into (R,E)-1-(4-((5-(2-fluoroethoxy)pyridin-2-yl)methyl)-2-methylpiperazin-1-yl)-3-(4-isocyano-2-((5-methyl-2H-tetrazol-2-yl)methyl)phenyl)prop-2-en-1-one through a palladium mediated cyanation reaction. [¹¹C]HCN may be converted into [¹¹C]CuCN and reacted with (R,E)-1-(4-((5-(2-fluoroethoxy)pyridin-2-yl)methyl)-2-methylpiperazin-1-yl)-3-(4-iodo-2-((5-methyl-2H-tetrazol-2-yl)methyl)phenyl)prop-2-en-1-one through the Rosenmund-von Braun reaction.

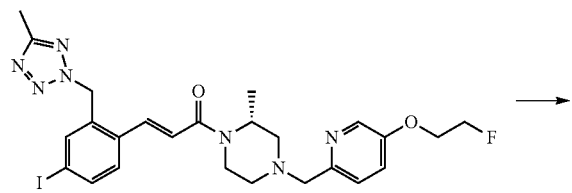

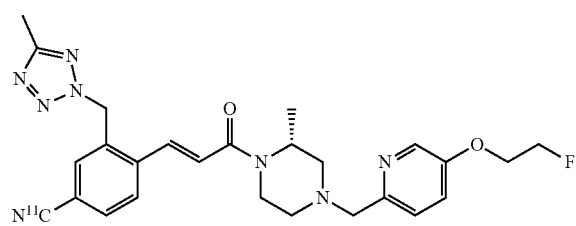

6) Synthesis of [¹¹C]OCH₃ examples, e.g. (R,E)-1-(4-((5-(2-fluoroethoxy)pyridin-2-yl)methyl)-2-methylpiperazin-1-yl)-3-(4-[¹¹C]methoxy-2-((5-methyl-2H-tetrazol-2-yl)methyl)phenyl)prop-2-en-1-one

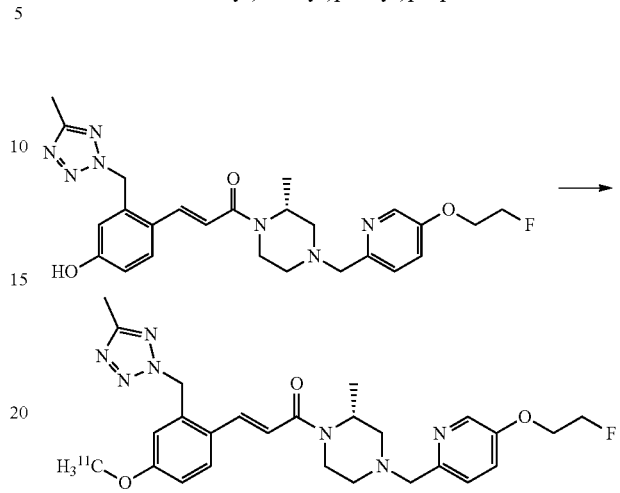

The precursor of the title compound, 4R,E)-1-(4-((5-(2-fluoroethoxy)pyridin-2-yl)methyl)-2-methylpiperazin-1-yl)-3-(4-hydroxy-2-((5-methyl-2H-tetrazol-2-yl)methyl)phenyl)prop-2-en-1-one), may be obtained according to the synthetic scheme given for example 1 using (3-bromo-4-(bromomethyl)phenoxy)triisopropylsilane prepared from the corresponding alcohol and 5-methyl-2H-tetrazole to provide (R,E)-1-(4-((5-(2-fluoroethoxy)pyridin-2-yl)methyl)-2-methylpiperazin-1-yl)-3-(2-((5-methyl-2H-tetrazol-2-yl)methyl)-4-((triisopropylsilyoxy)phenyl)prop-2-en-1-one. The subsequent deprotection of the phenol using TBAF in THF may provide the required precursor. The methylation of (R,E)-1-(4-((5-(2-fluoroethoxy)pyridin-2-yl)methyl)-2-methylpiperazin-1-yl)-3-(4-hydroxy-2-((5-methyl-2H-tetrazol-2-yl)methyl)phenyl)prop-2-en-1-one using [¹¹C]CH₃I in the presence of a base may lead to the title compound.

7) Synthesis of [¹²³I]-, [¹²⁴I]- or [¹⁴³I]-containing examples, e.g. (R,E)-1-(4-((5-(2-fluoroethoxy)pyridin-2-yl)methyl)-2-methylpiperazin-1-yl)-3-(4-[¹²³I]iodo-2-((5-methyl-2H-tetrazol-2-yl)methyl)phenyl)prop-2-en-1-one

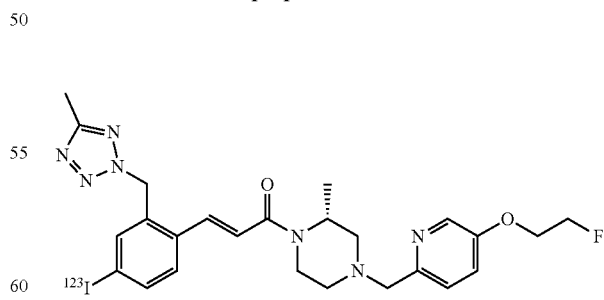

A stannane precursor may be prepared by reacting (R,E)-1-(4-((5-(2-fluoroethoxy)pyridin-2-yl)methyl)-2-methylpiperazin-1-yl)-3-(4-iodo-2-((5-methyl-2H-tetrazol-2-yl)methyl)phenyl)prop-2-en-1-one with bis(tributyltin) in the presence of a palladium catalyst such as Pd(PPh₃)₄:

Biological Data

The compounds described herein are ATX inhibitors and may be tested in the following assays.

Reagents—LPC (oleoyl (18:1)) was purchased from Avanti Polar Lipids (Alabaster, Ala.) and solubilized in methanol to 20 mM. Amplex Red was obtained from Invitrogen Life Technologies (Paisley, UK) and dissolved in DMSO to 10 mM. Choline oxidase and horseradish peroxidase (HRP) were obtained from Sigma Aldrich (Dorset, UK) and dissolved in HBSS to 20 U/ml and 200 U/ml respectively. All reagents were stored at −20° C. in single use aliquots. All experimental measurements were performed in assay buffer made up immediately prior to use (HBSS, 0.01% BSA essentially fatty acid free).

Protein—Recombinant human ATX was prepared at Novartis (Basel, CH) in a human embryonic kidney (HEK) cell preparation, and stored in single use aliquots of 26 mg/ml (26 μM) stocks stored at −80° C.

Method—All experimental measurements should be performed in black 384 well polystyrene (low volume, round bottom, Corning (3676)) plates. PerkinElmer EnVision (Fluorescence Intensity/Absorbance Monochromator) or Tecan Infinite 200 PRO series plate reader was used to detect change in fluorescent intensity.

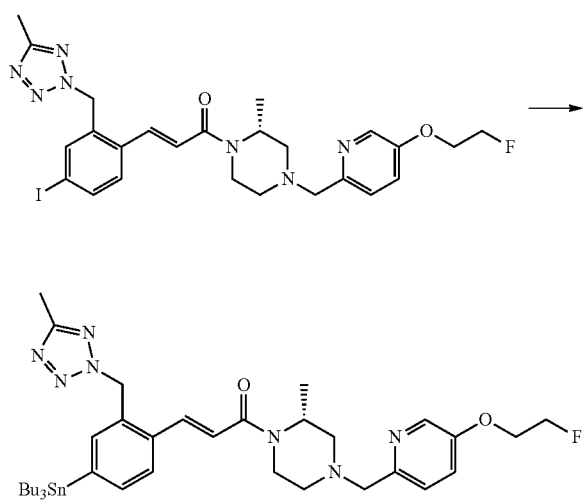

The treatment of (R,E)-1-(4-((5-(2-fluoroethoxy)pyridin-2-yl)methyl)-2-methylpiperazin-1-yl)-3-(2-((5-methyl-2H-tetrazol-2-yl)methyl)-4-(tributylstannyl)phenyl)prop-2-en-1-one with [$^{123}$I]NaI, [$^{124}$I]NaI or [$^{131}$I]NaI in the presence of a oxidizing agent such as chloramine-T may yield the title compounds (*I=[$^{123}$I], [$^{124}$I], or [$^{131}$I])

Assessing ATX inhibition—ATX activity was determined by measurement of released choline in reactions containing ATX (10 nM), choline oxidase (0.1 U/ml), HRP (100 U/ml), amplex red (50 μM) and LPC 18:1 (10 μM). Compounds of the invention should be prepared as 10 point serial dilutions from 1 μM in duplicate and pre-incubated with ATX at 37° C. for 20 minutes prior to the addition of remaining reagents. The liberated choline was measured from changes in fluorescence intensity (λex 530 nm, λm 590 nm) of the product resurofin at 37° C. every 2 minutes over a 40-minute period. ATX activity was measured as a slope of the linear portion of the progress curve, typically between 14 to 24 minutes.

Data analysis—Slope data was exported to Graphpad prism (Graphpad software, San Diego, Calif.) where data was fitted to equation 1.

$$Y = \text{Bottom} + (\text{Top} - \text{Bottom})/(1 + 10^{((\text{Log IC50} - X)*\text{HillSlope})}) \qquad \text{Equation 1}$$

$IC_{50}$ values were determined from the concentration of compound that reduced the total activity by 50% and represent the mean of n≥2.

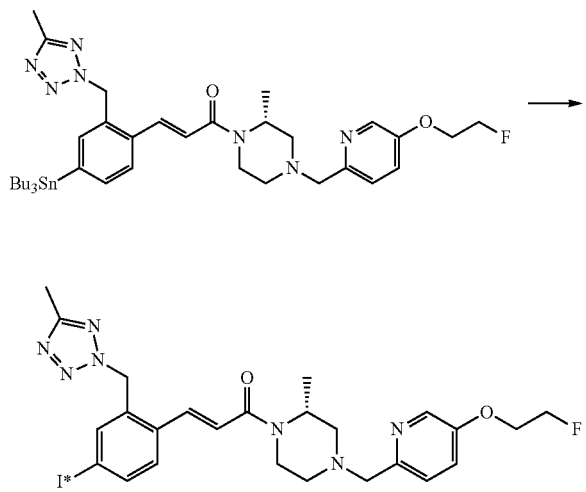

| Compound | IC50 |
|---|---|
|  | 3 nM |

| Compound | IC50 |
|---|---|
| 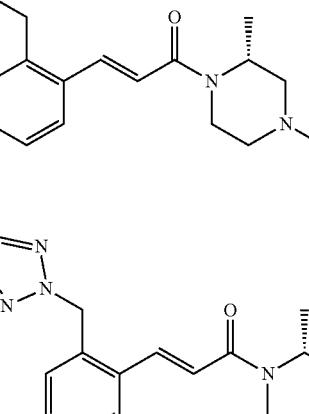 | 5 nM |
| | 4 nM |
| 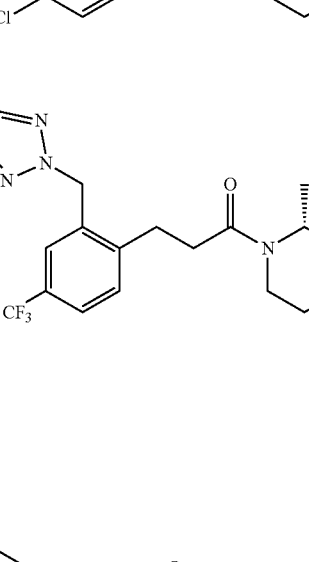 | 2 nM |
| 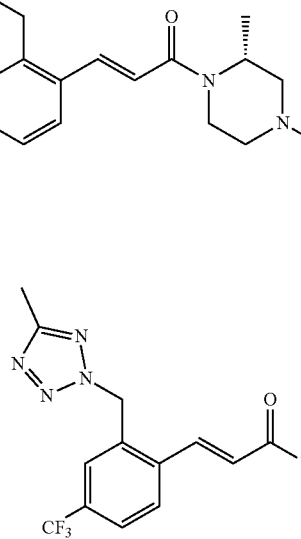 | 6 nM |
|  | 1.4 nM |

| Compound | IC50 |
|---|---|
| 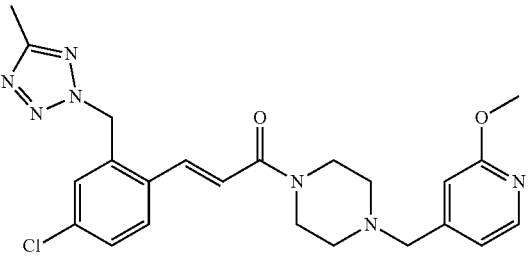 [SMILES: COc1cc(CN2CCN(C(=O)/C=C/c3ccc(Cl)cc3Cn3nnc(C)n3)CC2)ccn1] | 13  nM |

The invention claimed is:
1. A compound of the general Formula (I)

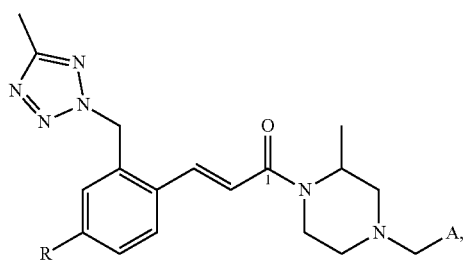

and/or a pharmaceutically acceptable salt thereof, wherein R is halogen, —CF$_3$, —OCF$_3$, —OCH$_3$, —CH$_3$ or CN; and A is a pyridinyl or oxazolyl group substituted with at least one substituent selected from halo-(C$_{1-6}$-alkyl), halo-(C$_{1-3}$-alkyl)oxy(C$_{2-4}$-alkyl), or halo-(C$_{1-3}$-alkyl)oxy (C$_{2-4}$-alkyl) oxy(C$_{2-4}$-alkyl) wherein compound of formula (I) contains at least one atom chosen from $^{3}$H, $^{18}$F, $^{123}$I, $^{124}$I, $^{125}$I, $^{127}$I, $^{131}$I, $^{11}$C, or $^{14}$C.

2. A compound according to claim 1 that contains $^{3}$H.

3. A compound according to claim 1 wherein R is —CF$_3$ or —OCF$_3$.

4. A compound according to claim 3 that contains at least one $^{18}$F.

5. A compound according to claim 1 wherein R is halogen.

6. A compound according to claim 5 wherein R is chosen from $^{18}$F, $^{19}$F, $^{123}$I $^{124}$I, $^{125}$I, $^{127}$I or $^{131}$I.

7. A compound according to claim 1 wherein A contains at least one of $^{18}$F, $^{19}$F, $^{123}$I, $^{124}$I, $^{125}$I, $^{127}$I or $^{131}$I.

8. A compound according to claim 1, wherein the carbon atom numbered "1" is chosen from $^{11}$C, $^{12}$C or $^{14}$C.

9. A compound selected from the group consisting of

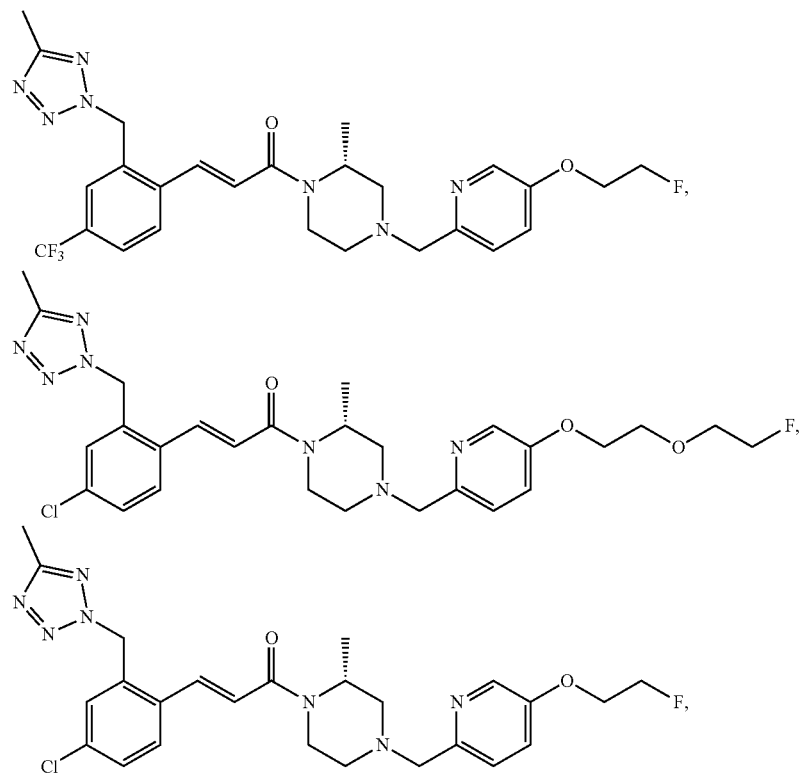

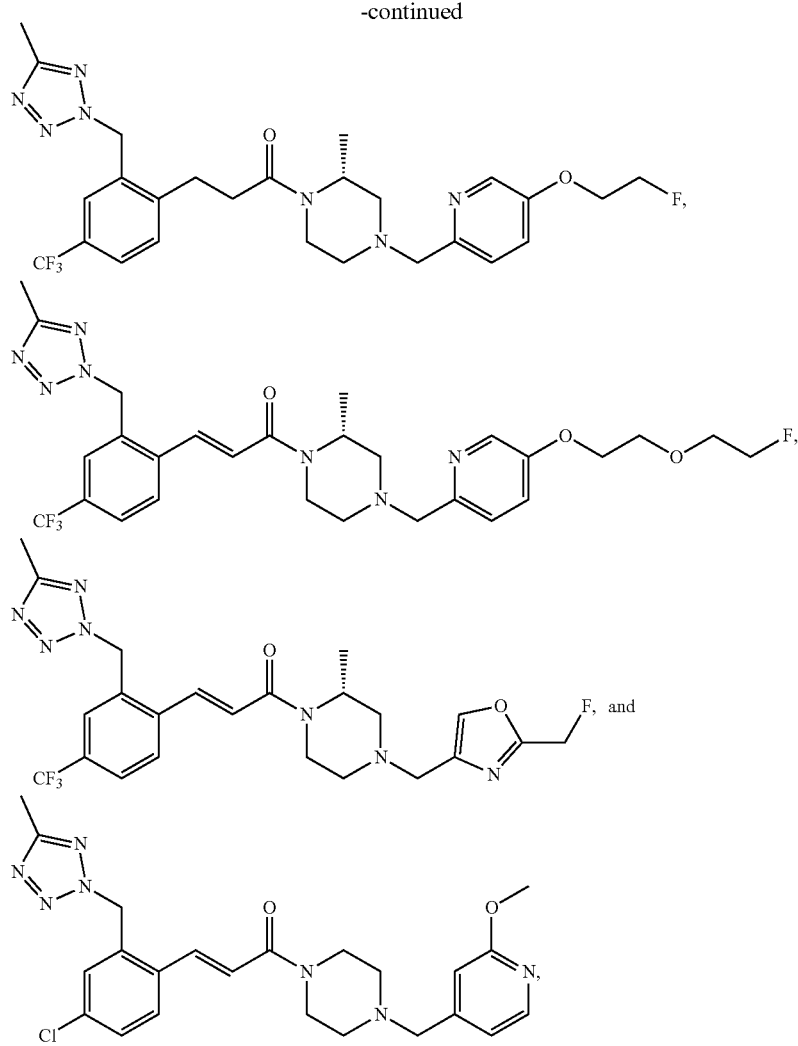

and/or a pharmaceutically acceptable salt thereof wherein compound contains at least one atom chosen from $^3$H, $^{18}$F, $^{123}$I, $^{124}$I, $^{131}$I, $^{11}$C, or $^{14}$C.

10. A method for the detection of autotaxin in a subject in recognized need thereof, said method comprising: (i) administration of a radiolabelled compound of formula (I) according to claim 1, or a pharmaceutically acceptable salt thereof to said subject; and (ii) detecting uptake of said compound by in vivo PET or SPECT imaging.

11. A composition comprising a compound according to claim 1 or a pharmaceutically acceptable salt thereof.

12. A composition according to claim 11 suitable for use in PET imaging.

* * * * *